US006587540B1

(12) United States Patent
Johnson et al.

(10) Patent No.: US 6,587,540 B1
(45) Date of Patent: Jul. 1, 2003

(54) APPARATUS AND METHOD FOR IMAGING OBJECTS WITH WAVEFIELDS

(75) Inventors: Steven A. Johnson; David T. Borup; James Wiskin; Michael J. Berggren, all of Salt Lake City, UT (US)

(73) Assignee: Techniscan, Inc., Salt Lake City, UT (US)

( * ) Notice: Subject to any disclaimer, the term of this patent is extended or adjusted under 35 U.S.C. 154(b) by 0 days.

(21) Appl. No.: 09/471,106

(22) Filed: Dec. 21, 1999

Related U.S. Application Data

(63) Continuation-in-part of application No. 08/706,205, filed on Aug. 29, 1996, now abandoned, which is a continuation-in-part of application No. 08/486,971, filed on Jun. 22, 1995, now abandoned, which is a continuation-in-part of application No. 07/961,768, filed on Oct. 14, 1992, now Pat. No. 5,588,032.

(51) Int. Cl.$^7$ ................................................. A61B 6/63
(52) U.S. Cl. ............................................. 378/62; 378/4
(58) Field of Search .......................... 378/4, 8, 62, 87, 378/901

(56) References Cited

U.S. PATENT DOCUMENTS 6,005,916 A * 12/1999 Johnson et al. ............... 378/87

OTHER PUBLICATIONS

P.R. Williamson, Tomographic inversion in reflection seismology, Geophys. J. Int. 100, pp. 255–274, 1990.
W.W. Kim, D.T. Borup, S.A. Johnson, M.J. Berggren, and Y. Zhou, "Accelerated Inverse Scattering Algorithms for Higher Contrast Objects," in 1987 IEEE Ultrasonics Symposium, 903–906, (IEEE Cat. No. 87ch2492–7).

S.J. Norton, "Iterative Seismic Inversion," Geophysical Journal, No. 94, pp. 457–468 (1988).
T.K. Sarkar, E. Arkas, and S.M. Rao (1986) "Application of FFT and the Conjugate Gradient Method for the Solution of Electromagnetic Radiation from Electrically Large and Small Conducting Bodies," IEEE Trans. Antennas Propagat., vol. AP–34, pp. 635–640, May.
R.J. Wombel and M.A. Fiddy (1988), "Inverse Scattering Within the Distorted–wave Born Approximation," Inverse Problems 4 (1988).
Y. Zhou, S.A. Johnson, M.J. Berggren, B. Carruth, and W.W. Kim, "Constrained Reconstruction of Object Acoustic Parameters from Noisy Ultrasound Scattering Data," Proc. of the IEEE 1987 Ultrasonics Symposium pp. 897;901 (1987).
Kostas T. Ladas and A. J. Devaney, "Iterative Methods in Geophysical Diffraction Tomography," Inverse Problems 8 (1992).

(List continued on next page.)

*Primary Examiner*—David V. Bruce
(74) *Attorney, Agent, or Firm*—Lee & Hayes, PLLC

(57) ABSTRACT

This invention describes a method for increasing the speed of the parabolic marching method by about a factor of 256. Firstly, to form true 3-D images or 3-D assembled from 2-D slices. Secondly, the frequency of operation can be increased to 5 MHz to match the operating frequency of reflection tomography. This allow the improved imaging of speed of sound which in turn is used to correct errors in focusing delays in reflection tomography imaging. This allows reflection tomography to reach or closely approach its theoretical spatial resolution of ½ to ¾ wave lengths. A third benefit of increasing the operating frequency of inverse scattering to 5 MHz is the improved out of topographic plane spatial resolution. This improves the ability to detect small lesions. It also allow the use of small transducers and narrower beams so that slices can be made closer to the chest wall.

26 Claims, 16 Drawing Sheets

OTHER PUBLICATIONS

M.J. Berggren, S.A. Johnson, W.W. Kim, D.T. Borup, R.S. Eidens and Y. Zhou, "Acoustic Inverse Scattering Images from Simulated Higher Contrast Objects and from Laboratory Test Objects," Acoustical Imaging 16, Chicago, Illinois, Jun. 1987.

Brent S. Robinson and James F. Greenleaf, "An Experimental Study of Diffraction Tomography Under the Born Approximation," Acoustical Imaging 18, No. 18, Jun. 1990.

M.J. Berggren, S.A. Johnson, B.L. Carruth, W.W. Kim, F. Stenger and P.L. Kuhn, "Performance of Fast Inverse Scattering Solutions for the Exact Helmholtz Equation Using Multiple Frequencies and Limited Views," Acoustical Imaging 15, Halifax, Nova Scotia, Jul. 1986.

W.W. Kim, S.A. Johnson, M.J. Berggren, F. Stenger and C.H. Wilcox, "Analysis of Inverse Scattering Solutions from Single Frequency, Combined Transmission and Reflection Data for the Helmholtz and Riccati Exact Wave Equations," Acoustical Imaging 15, pp. 359–369, Plenum Press (1987).

E.J. Ayme–Bellegarda and T.M. Habashy, "Forward Ultrasonic Scattering from Multidimensional Solid or Fluids Inclusions Buried in Multilayered Elastic Structures," IEEE Trans. Ultras., Ferro., and Freq. Cont., vol 39, No. 1, Jan. 1992.

E.J. Ayme–Bellegarda, and T.M. Habashy, "Ultrasonic Inverse Scattering of Multidimensional Objects Buried in Multilayered Elastic Background Structures," IEEE Trans. Ultras., Ferro, and Freq. Cont., vol 39, No. 1, Jan. 1992.

J.K. Cohen and F.G. Hagin, "Velocity Inversion Using a Stratified Reference," Geophysics, 50, 11, 1985.

E. Crase, A. Pica, M. Noble, J. McDonald, and A. Tarantola, "Robust Elastic Nonlinear Waveform Inversion: Application to Real Data," Geophysics, 55, 5 (May 1990).

Peter Mora, "Nonlinear Two–dimensional Elastic Inversion of Multioffset Seismic Data," Geophysics, vol. 52, 9, Sep. 1987.

G.S. Pan, R.A Phinney and R.I. Odom, "Full–waveform Inversion of Plane–wave Seismograms in Stratified Acoustic Media: Theory and Feasibility," Geophysics, vol. 53, 1 (1988).

G.R. Franssens, "Calculation of the Elasto–dynamic Green's Function in Layered Media by Means of a Modified Propagator Matrix Method," Geophys. J.R. astr. Soc. 1983.

B.L.N. Kennett and N.J. Kerry, "Seismic Waves in a Stratified Half Space," Geophys. J.R. astr. Soc. 57, pp. 557–583, 1979.

* cited by examiner

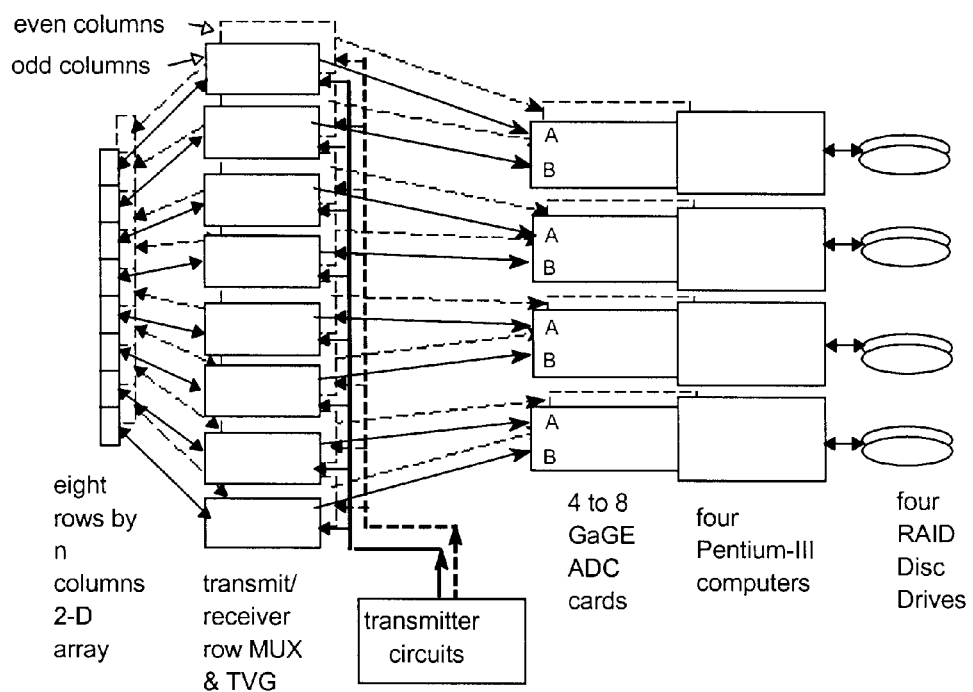
Figure 3.a

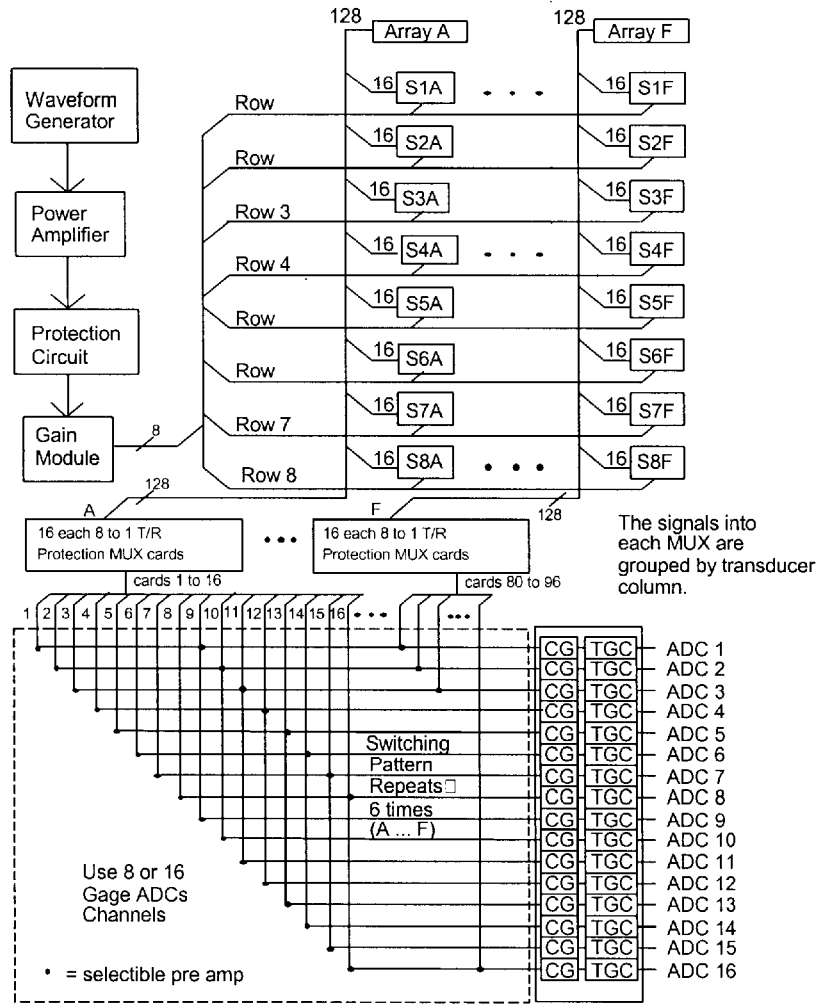
Figure 3.b
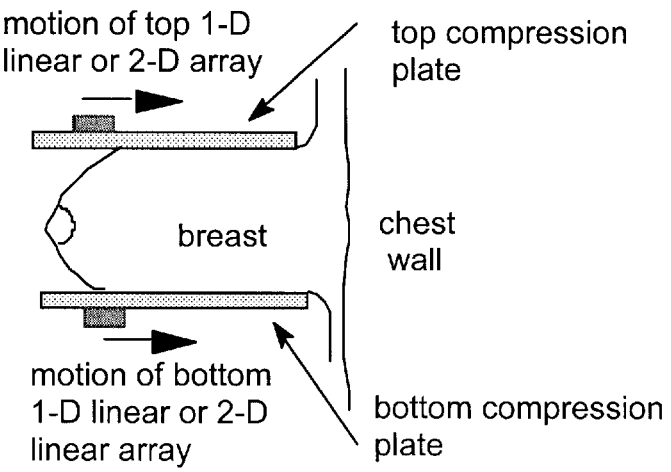
Figure 4.a

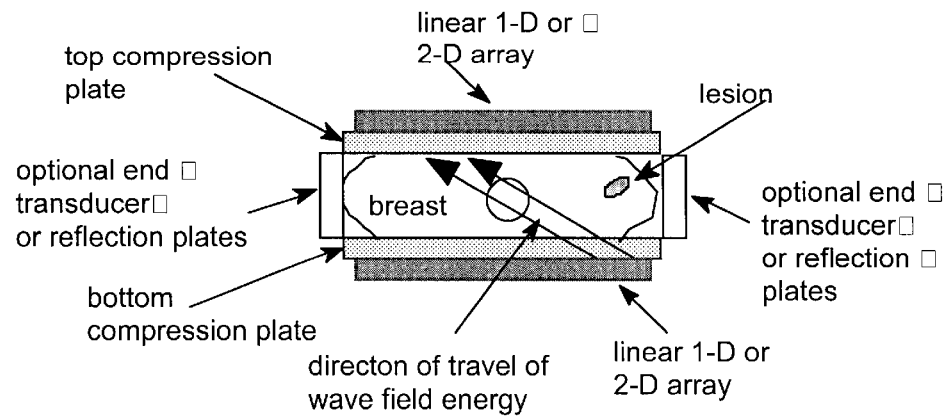
Figure 4.b
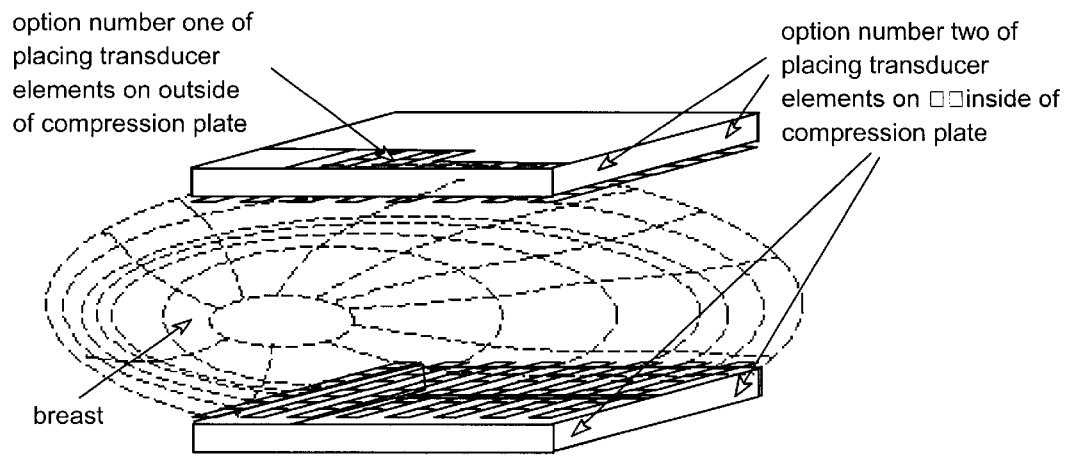
Figure 4.c

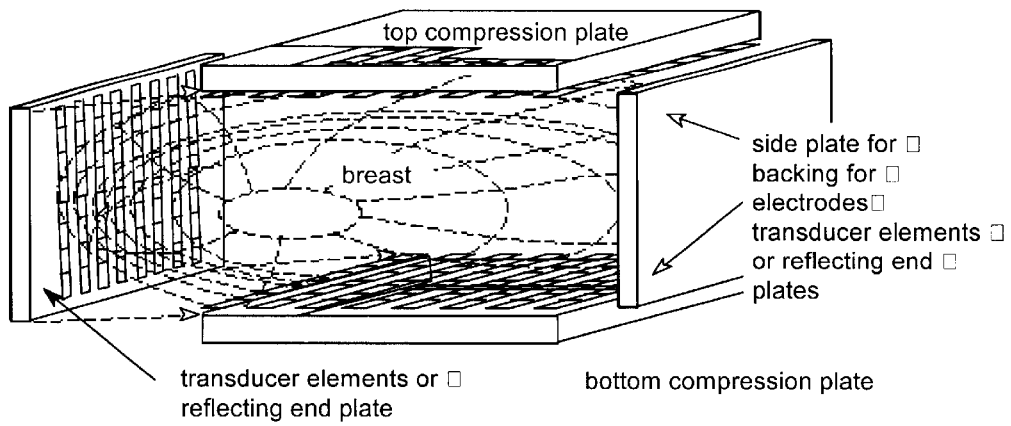
Figure 4.d
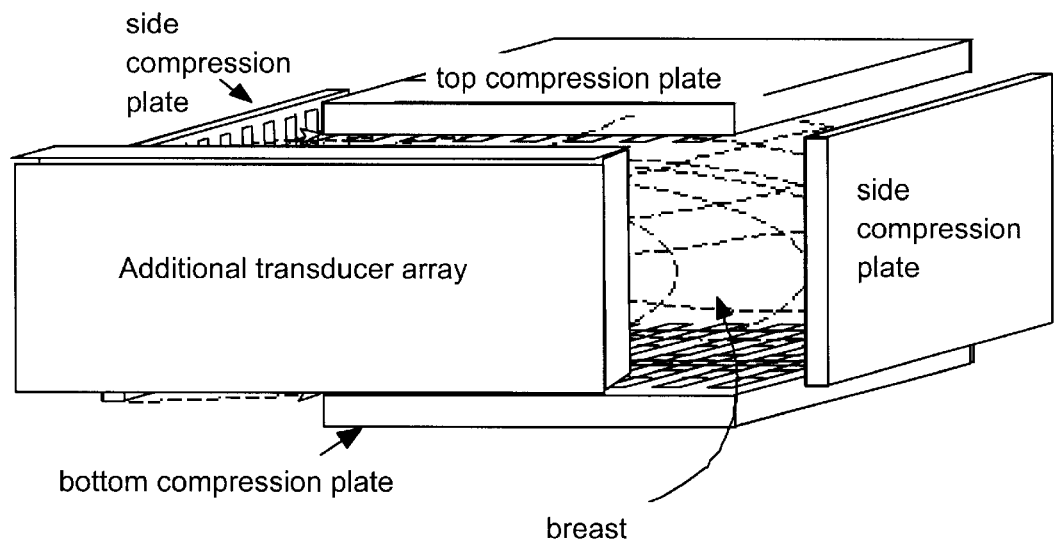
Figure 4.e

Figure 5.a.   Speed of sound model of a breast compressed between two plates as in a mammogram.

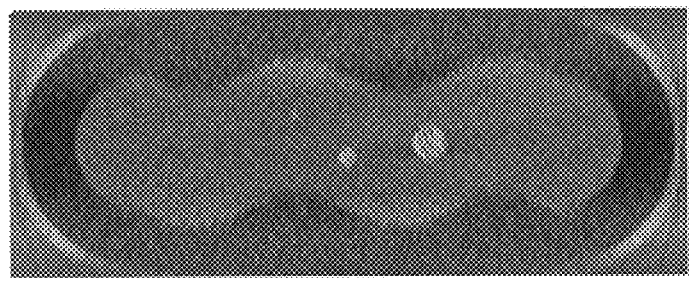

Figure 5.b   Reconstructed image of sound speed (including fluctuations) using a 1/2 wavelength pixel parabolic inverse scattering algorithm.

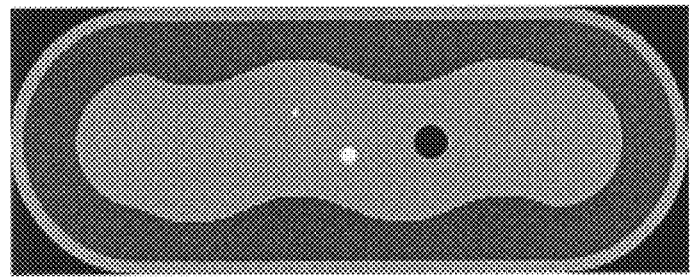

Figure 5.c.   Attenuation model using a 1/2 wavelength pixel parabolic inverse scattering algorithm.

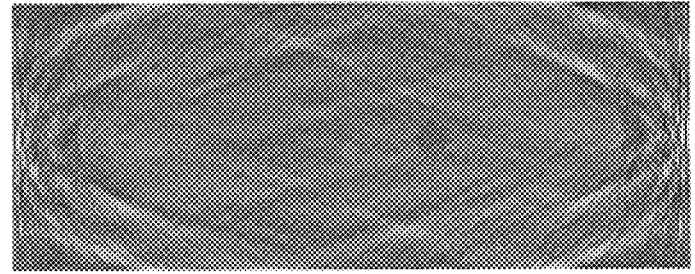

Figure 5.d.   Reconstructed image of the acoustic attenuation using a 1/2 wavelength pixel parabolic inverse scattering algorithm.

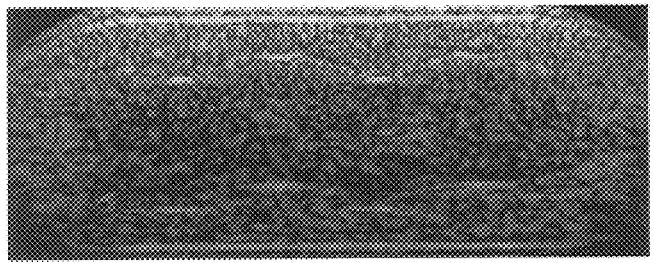
Figure 5.e.  B-scan image created from simulated data for model defined in Figs. 1-2 with scattering from fluctuation in speed of sound.
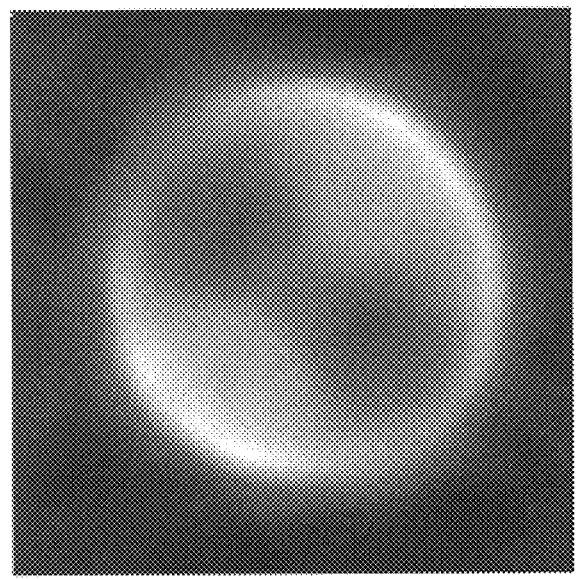
Figure 6.a.  "Time of flight image" i.e., speed of sound map (image) obtained from real time of flight data collected on a laboratory scanner through application of a time of flight CT algorithm.

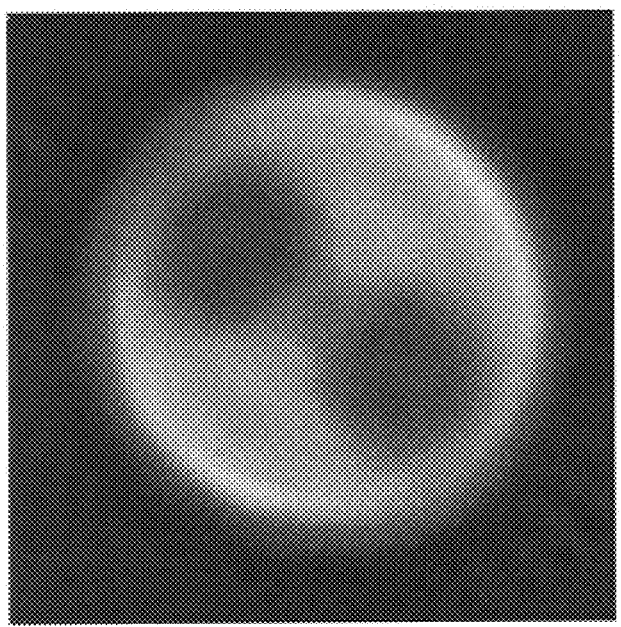
Figure 6.b. Sound speed map (image) obtained after 15 steps of new fast 2 wavelength pixel algorithm starting with the same data by time of flight CT algorithm.
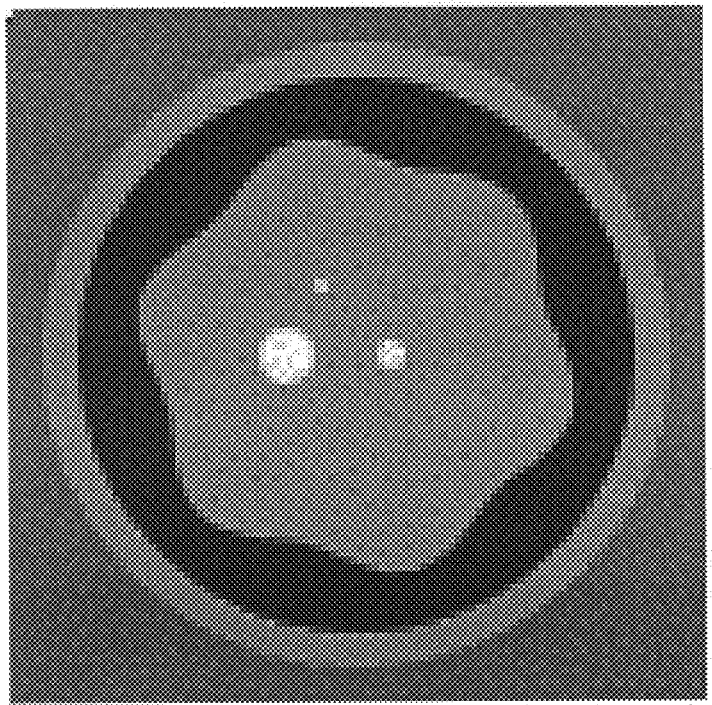
Figure 7.a Normalized true speed of sound image, $[c_0/c(x,y) - 1]$, used to generate simulated data to test 2 wavelength pixel algorithm.

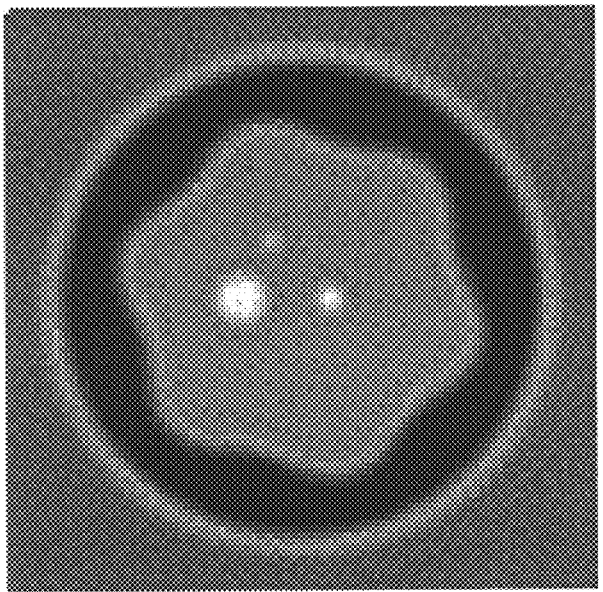
Figure 7.b  Normalized image, $[c_0/c(x,y) - 1]$, reconstructed by the 2 wavelength pixel algorithm.
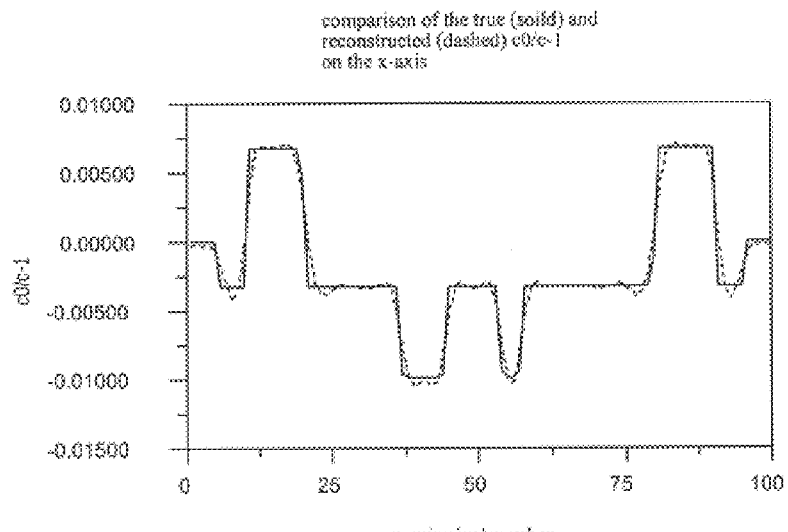
Figure 7.c  Sampled true and reconstructed 2 wavelength pixel images through horizontal, center line.

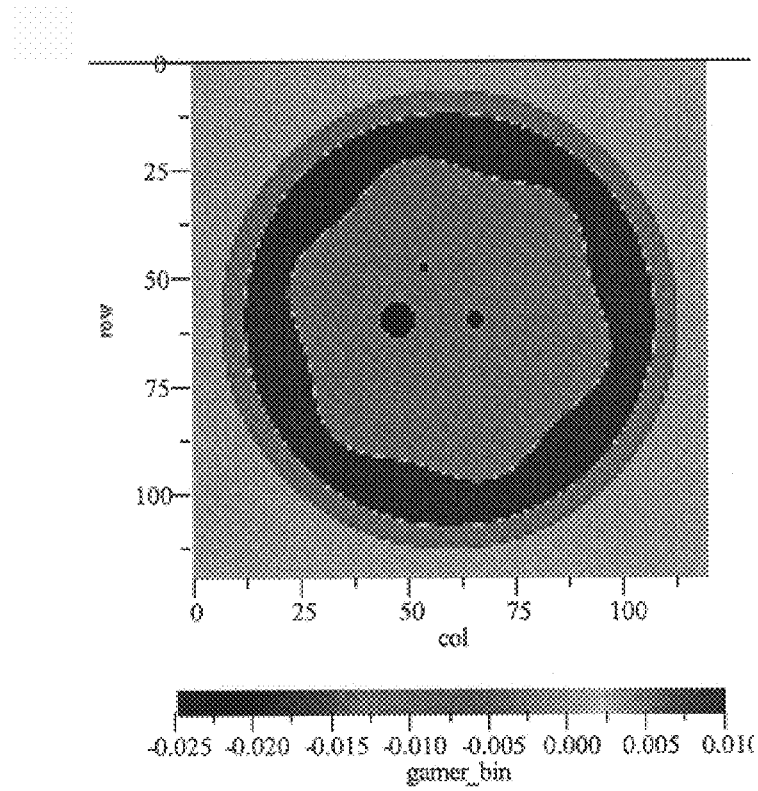
Figure 8.a    A 120 by 120 pixel image of Re(g) for the true object.
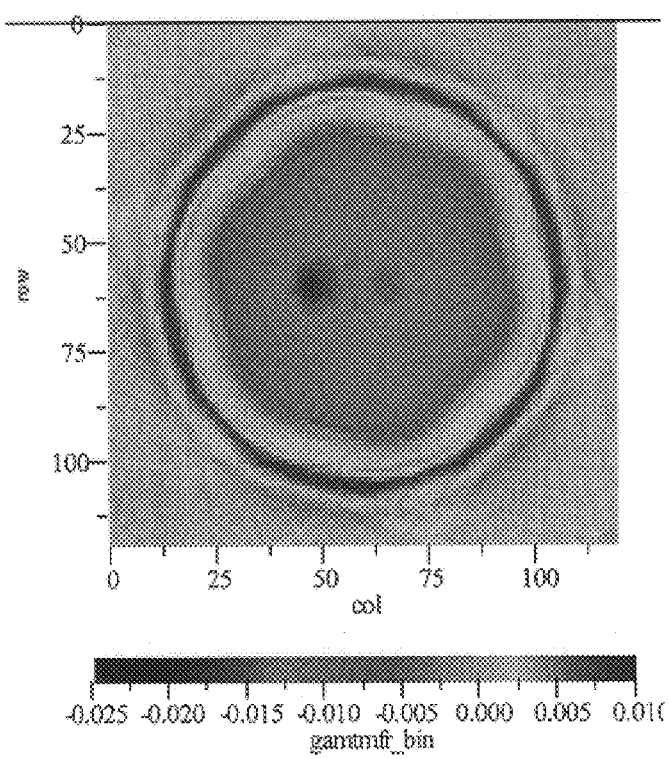
Figure 8.b    A 120 by 120 pixel image of the Re(g) reconstructed using the straight line, time of flight CT algorithm.

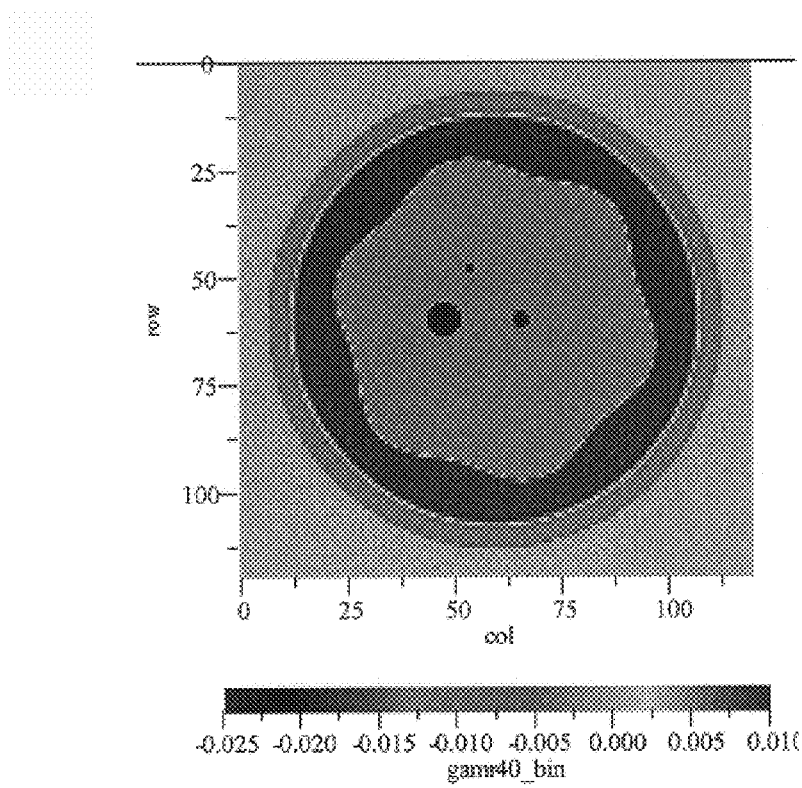
Figure 8.c    A 120 by 120 pixel image image made by new fast parabolic algorithm.
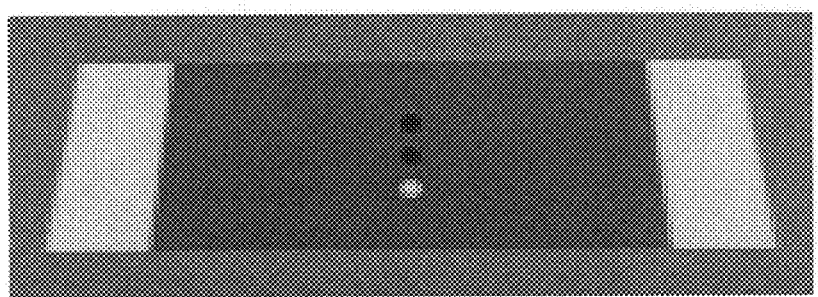
Figure 9.a    True 3-D speed of sound x-y image for breast cancer model on plane y=75.

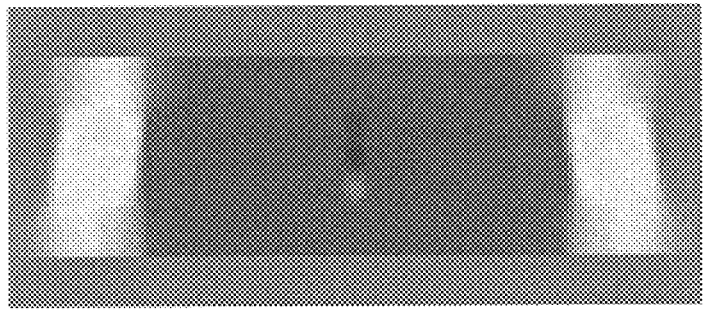
Figure 9.b    Parabolic reconstructed 3-D speed of sound x-y image for breast cancer model on plane y=75.
Figure 10.a    Commercial B-scan Image of the cancerous breast tissue.

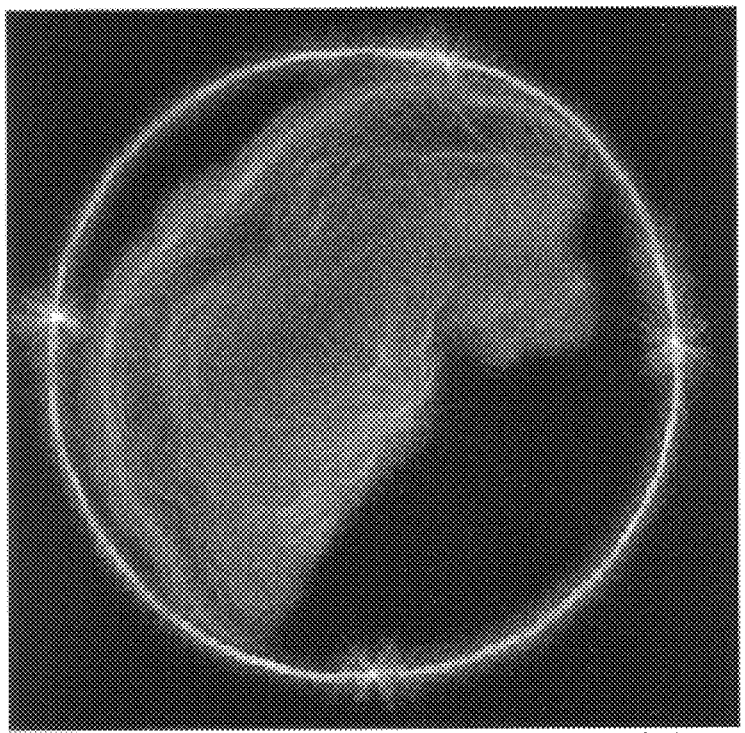
Figure 10.b  Comparison image of reflection tomography image of corresponding slice of the cancerous breast tissue shown in the companion B-scan image.

APPARATUS AND METHOD FOR IMAGING OBJECTS WITH WAVEFIELDS

RELATED APPLICATIONS

This patent refers to U.S. patent application Ser. No. 08/972,101, filed on Nov. 17, 1997, which issued on Dec. 21, 1999 as U.S. Pat. No. 6,005,916, which is a continuation of U.S. patent application Ser. No. 08/706,205, filed on Aug. 29, 1996, now abandoned which is a continuation-in-part of U.S. patent application Ser. No. 08/486,971 filed on Jun. 22, 1995, now abandoned which is a continuation-in-part of U.S. patent application Ser. No. 07/961,768 filed on Oct. 14, 1992, now U.S. Pat. No. 5,588,032, all of which are incorporated herein by reference.

INCORPORATION BY REFERENCE

Material on one (1) compact disc accompanying this patent and labeled COPY 1, a copy of which is also included and is labeled as COPY 2, is incorporated herein by reference. The compact disc has a software appendix thereon in the form of the following three (3) files:

(i) Appendix A.doc, Size: 16Kbytes, Created: Aug. 13, 2001;

(ii) Appendix B.doc, Size: 19Kbytes, Created: Aug. 13, 2001; and (iii) Appendix C.doc, Size: 1Kbytes, Created: Aug. 13, 2001.

BACKGROUND OP THE INVENTION

This invention is designed to provide improved imaging of bodies using wave field energy such as ultrasound energy, electromagnetic energy, elastic wave energy or Biot wave energy. In particular it is designed to provide improved imaging for medical diagnostic applications, for geophysical imaging applications, for environmental imaging applications, for seismic applications, for sonar applications, for radar applications and for similar applications were wave field energy is used to probe and image the interior of objects.

In particular, this invention has important applications to the field of medical diagnosis with specific value to improved breast cancer detection and screening. The present method of choice is mammography. This choice is not supported by outstanding performance of mammography, but rather because it is the most diagnostically effective for its present cost per exam. Another reason for the wide spread use of mammography is the inertia of changing to other modalities. It is known that hand-probe-based, clinical reflection ultrasound can match the performance of mammography in many cases, but only in the hands of specially trained ultrasound radiologists. Today and in the foreseeable future, there are more mammography machines and radiologists trained to use them than there are trained ultrasound radiologists that have access to high quality ultrasound scanners. Sophisticated breast cancer diagnostic centers use both mammography and ultrasound to compensate for weakness in either approach when used alone. When used alone, ultrasound and mammography require a biopsy to remove a sample of breast tissue for pathology lab analysis to determine whether a sampled lesion is cancerous or benign.

Even when mammography and ultrasound are used together the specificity for discriminating between cancer and fibrocystic condition or between cancerous tumor and a fibroadenoma is not high enough to eliminate the need for biopsy in 20 to 30 percent of lesions. Given that early diagnosis on breast cancer can insure survival and given that one woman in eight will have breast cancer in her life, it is important for the general population for cancer to be detected as early as possible. Detection on cancer in an early stage for biopsy is thus very important. However, biopsy of benign lesions is traumatic to the patient and expensive. A mammogram cost about $90 but a biopsy is about ten times more expensive. Thus it is important that a breast cancer diagnostic system have as high specificity and sensitivity to eliminate unnecessary biopsies. Increasing the rate of diagnostic true positives to near 100 percent will identify all lesions as a cancer that are cancer without the need to biopsy. But is also necessary to increase the rate of true negatives to near 100 percent to eliminate biopsy of benign lesions. Neither mammography or ultrasound or their joint use has provided the combination of sensitivity and specificity to eliminate biopsy or to detect all cancers early enough to insure long term survival after breast cancer surgery for all women that have had breast exams.

There does not seem to be any obvious improvements in present mammography or hand-probe-based, clinical reflection ultrasound that can significantly improve these statistics. However, there is reason to believe that inverse scattering ultrasound tomography or electric impedance tomography can provide improved diagnostic sensitivity or specificity when used separately or jointly with themselves and with ultrasound and/or mammography. Inverse scattering ultrasound imaging provides several advantages over present clinical reflection ultrasound that uses hand held ultrasound probes. A hand held probe is a transducer assembly that scans an area of the patient's body below the probe. Probes comprising mechanical scanning transducers and probes comprising electronically scanned arrays of transducer elements are both well developed technologies.

Inverse scattering has the following advantages over said clinical reflection ultrasound. Inverse scattering images have the following features: (1) two separate images can be made, one of speed of sound and one acoustic absorption; (2) these images are quantitative representation of actual acoustic bulk tissue properties; (3) the images are machine independent; (4) the images are operator independent; (5) the images are nearly free of speckle and other artifacts; (6) all orders of scattering tend to be used to enhance the images and do not contribute to artifacts or degrade the images; (7) the images of speed of sound and absorption create a separation of tissues into classes (fat, benign fluid filled cyst, cancer, and fibroadenoma), although the cancer and fibroadenoma values tend to overlap; (8) the speed of sound and acoustic absorption images have excellent spatial resolution of 0.3 to 0.65 mm at 5 MHz; and (9) the speed of sound images can be used to correct reflection tomography for phase aberration artifacts and improve ultrasound reflectivity spatial resolution. Inverse scattering easily discriminates fat from other tissues, while mammography and present clinical ultrasound can not.

Because of the similar values of speed of sound and acoustic absorption between cancer and fibrocystic condition (including fibroadenoma), it is not known whether inverse scattering will provide the required high lever of specificity to eliminate biopsy. Perhaps this performance could be achieved if inverse scattering were combined with reflection ultrasound or with mammography or with both.

A traditional problem with inverse scattering imaging is the long computing times required to make an image. Diffraction Tomography is a subset of inverse scattering that uses first order perturbation expansion of some wave equation. Diffraction Tomography is extremely rapid in image computation, but suffers the fatal flaw for medical imaging of producing images that are blurred and not of acceptable quality for diagnostic purposes. In out last patent application, we addressed the speed problem with inverse scattering and showed how to increase the calculation speed by two orders of magnitude over finite difference method or over integral equation methods. This speed up in performance was achieved by use of parabolic and other marching methods. This improvement in speed was sufficient to allow single slices to be collected at frequencies of 2 MHz using 3-D scattered data collected on a 2-D detector, but making a full 3-D image at once or from stacked 2-D slices would have required computing speed not available then and even mostly now.

Another imaging modality that has been investigated to detecting breast cancer is EIT (electrical impedance tomography). This modality has been investigated for many years and many of its features are well known. One of its great advantages for breast cancer detection is its high selectivity between cancer and fibrocystic conditions including fibroadenoma. Cancer has high electrical conductivity (low electrical impedance) while fibrocystic conditions and fibroadenoma have low electrical conductivity (high electrical impedance). However, EIT has poor spatial resolution. Also EIT requires the use of inversion algorithms similar (in a general sense) to those of inverse scattering. In addition EIT algorithms have mostly been used to make 2-D images. Work on making 3-D EIT images is less developed because of the increased computer run time of 3-D algorithms.

Other problems with mammography maybe listed, such as the pain associated with compressing the breast between two plates to reduce the thickness of the breast in order to improve image contrast and cancer detection potential. Another problem is accumulated ionizing radiation dose over years of mammography. It is true that a single mammogram has very low x-ray dose, especially with modem equipment. However, if mammograms are taken every year from age 40 or earlier, then by age 60 to 70 the accumulated dose begins to cause breast cancer. The effect is slight, and the benefits of diagnosis outweigh this risk. Nevertheless, it would be and advantage to eliminate this effect. Mammography is not useful in younger women (because of the greater density of their breasts) or older women with dense breasts (such as lactating women). About 15 percent of women have breasts so dense that mammography has no value and another 15 percent of women have breasts dense enough that the value of mammography is questionable. Thus 30 percent of all mammograms are of questionable or zero value because of image artifacts from higher than normal beast density.

SUMMARY OF THE INVENTION

This invention describes a method for increasing the speed of the parabolic marching method by about a factor of 256. This increase in speed can be used to accomplish a number of important objectives. Firstly, the speed can be used to collect data to form true 3-D images or 3-D assembled from 2-D slices. Speed allows larger images to be made. Secondly, the frequency of operation can be increased to 5 MHz to match the operating frequency of reflection tomography. This allows the improved imaging of speed of sound which in turn is used to correct errors in focusing delays in reflection tomography imaging. This allows reflection tomography to reach or closely approach its theoretical spatial resolution of 1/2 to 3/4 wave lengths. A third benefit of increasing the operating frequency of inverse scattering to 5 MHz is the improved out of tomographic plane spatial resolution. This improves the ability to detect small lesions. It also allow the use of small transducers and narrower beams so that slices can be made closer to the chest wall.

An additional benefit of the inversion is the flexibility to make trade offs between pixel size, operating frequency and spatial resolution. Increasing pixel size slightly at a fixed operating frequency decreased spatial resolution by a proportional small amount but makes a dramatic decrease in computation time. Like wise, both the operation frequency and the pixel size can be increased to produce no change in spatial resolution, but provide other benefits of higher operating frequency as discussed above.

A further benefit of the inversion is the more rapid convergence to the global minima. This is especially important at higher operating frequencies such as 5 MHz. This invention allows the elimination or greatly reduced influence of local minima on optimization methods for finding inverse scattering solutions.

Additional objects and advantages of the invention will be set forth in the description which follows, and in part will be obvious from the description, or may be learned by practice of the invention. The objects and advantages of the invention may be realized and obtained by means of the instruments and combinations particularly pointed out in the appended claims. These and other objects and features of the invention will become more fully apparent from the following description and appended claims, or may be learned by the practice of the invention as further set forth hereinafter.

BRIEF DESCRIPTION OF THE DRAWINGS

In order that the manner un which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 3.$a$: Block Diagram total waterbath scanner system

FIG. 3.$b$: Block Diagram of transmit and receive MUX

FIG. 4.$a$: Side view of ultrasound compression plate scanner for transmission inverse scattering and reflection ultrasound FIG. 4.$b$: End View of ultrasound compression plate scanner for transmission inverse scattering and reflection ultrasound.

FIG. 4.$c$: Isometric view of compression plate scanner showing options for placing transducer elements either inside of outside of the top and bottom compression plates.

FIG. 4.$d$: Isometric view of compression plate scanner showing options for placing side compression plates with optional transducer elements either inside of outside of the side compression plates.

FIG. 4.$e$: Isometric view of compression plate scanner showing option for placing front compression plates with optional transducer elements either inside of outside of the front compression plates.

FIG. 5.$a$: Speed of sound model of a breast compressed between two plates as in a mammogram.

FIG. 5.b: Reconstructed image of sound speed (including fluctuations) using a ½ wavelength pixel parabolic inverse scattering algorithm.

FIG. 5.c: Attenuation model using a ½ wavelength pixel parabolic inverse scattering algorithm.

FIG. 5.d: Reconstructed image of the acoustic attenuation using a ½ wavelength pixel parabolic inverse scattering algorithm.

FIG. 5.e: B-scan image created from simulated data for model defined in FIGS. 1–2 with scattering from fluctuation in speed of sound.

FIG. 6.a: "Time of flight image" i.e., speed of sound map (image) obtained from real time of flight data collected on a laboratory scanner through application of a time of flight CT algorithm.

FIG. 6.b: Sound speed map (image) obtained after 15 steps of new fast 2 wavelength pixel algorithm starting with the same data by time of flight CT algorithm.

FIG. 7.a: Normalized true speed of sound image, $[c_o/c(x,y)-1]$, used to generate simulated data to test 2 wavelength pixel algorithm.

FIG. 7.b: Normalized image, $[c_o/c(x,y)-1]$, reconstructed by the 2 wavelength pixel algorithm.

FIG. 7.c: Sampled true and reconstructed 2 wavelength pixel images through horizontal, center line.

FIG. 8.a: A 120 by 120 pixel image of Re(g) for the true object.

FIG. 8.b: A 120 by 120 pixel image of the Re(g) reconstructed using the straight line, time of flight CT algorithm.

FIG. 8.c: A 120 by 120 pixel image made by new fast parabolic algorithm.

FIG. 9.a: True 3-D speed of sound x-y image for breast cancer model on plane y=75.

FIG. 9.b: Parabolic reconstructed 3-D speed of sound x-y image for breast cancer model on plane y=75.

FIG. 10.a: Commercial B-scan Image of the cancerous breast tissue.

FIG. 10.b: Comparison image of reflection tomography image of corresponding slice of the cancerous breast tissue shown in the companion B-scan image.

DETAILED DESCRIPTION OF THE PREFERRED EMBODIMENTS

Embodiments within the scope of the present invention also include computer-readable media having computer-executable instructions or data structures stored thereon. Such computer-executable media can comprise RAM, ROM, EEPROM, CD-ROM or other optical disk storage, magnetic disk storage or other magnetic storage devices, or any other medium which can be used to store desired computer-executable instructions or data structures and which can be accessed by a general purpose or special purpose computer. When information is transferred or provided over a network or another communications connection to a computer, the computer properly views the connection as a computer-readable medium. Thus, such connection is also properly termed a computer-readable medium. Combinations of the above should also be included within the scope of computer readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which the invention may be implemented. Although not required, the invention can be implements in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked through a communications network. In the distributed computing environment, program modules may be located in both local and remote memory storage devices.

Figure 1:
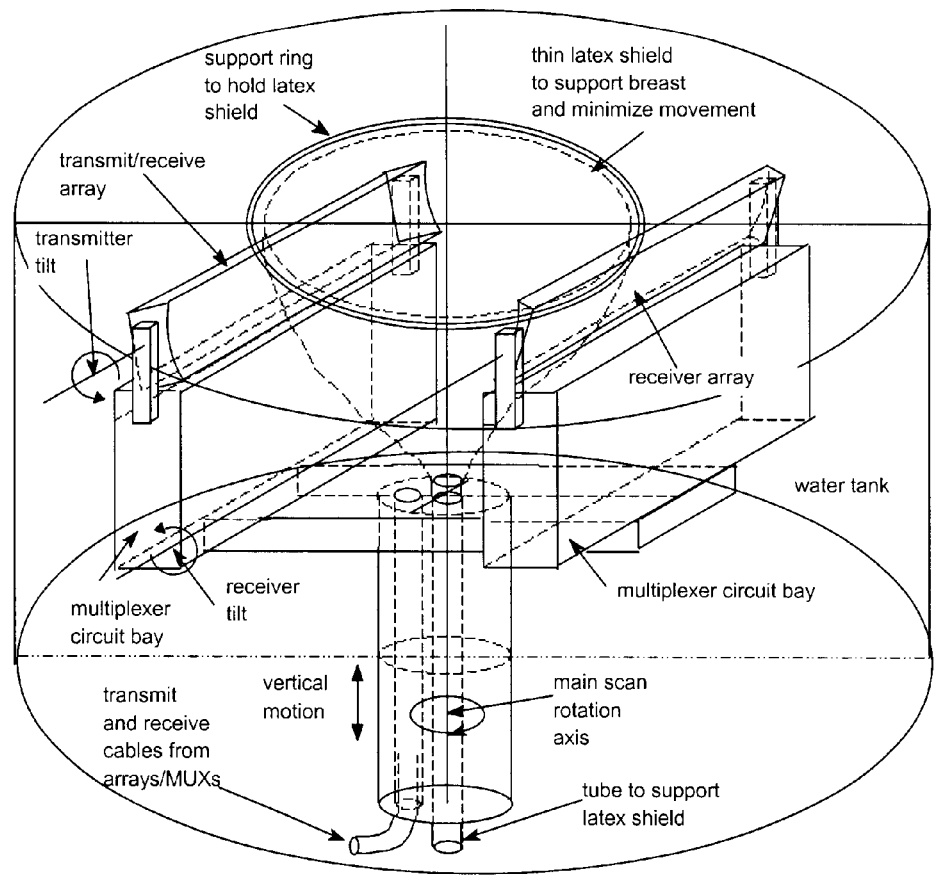
FIG. 1: Illustration of the water bath scanner and the associated two transducer arrays.

Water Bath Scanner compatible with Reflection tomography and Large Pixel Inverse Scattering General features of the proposed water bath scanner are shown in FIG. 1. It is seen that the general architecture is a pair of 2-D arrays (actually 1.75-D arrays) that are rotated about a vertical axis below the water surface. Each array acts as both a transmitter and a receiver in both pulse echo mode (13-scan and reflection tomography) and in transmission mode (inverse scattering tomography). This arrangement allows a complete 360 degree tomographic scan to be obtained in only 180 degrees of rotation of the array. Each array can be tilted up to image features close to the chest wall. The respective tilt axes are mutually parallel. The arrays as a group can be raised and lowered to image different slices of the breast. An optional latex rubber shield (or a woven nylon stocking-like shield) holds the breast stationary to minimize motion artifacts during scanning. The shield is held at the top of the water tank by a ring and at the bottom by a tub that passes through the hole in the rotation shaft.

Figure 2:
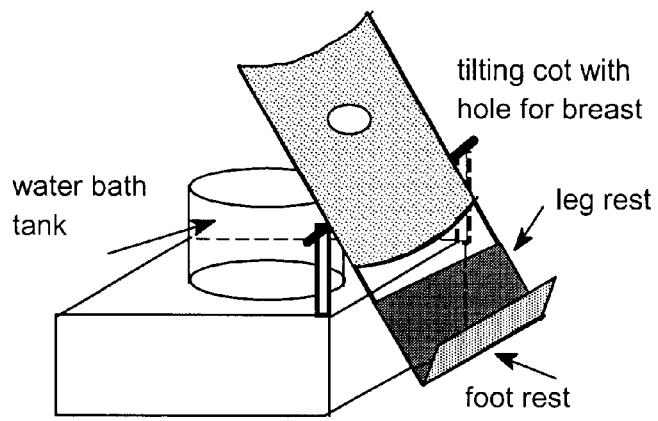
FIG. 2: Tilting cot for patient positioning and scanning using water bath scanner.
Figure 11:
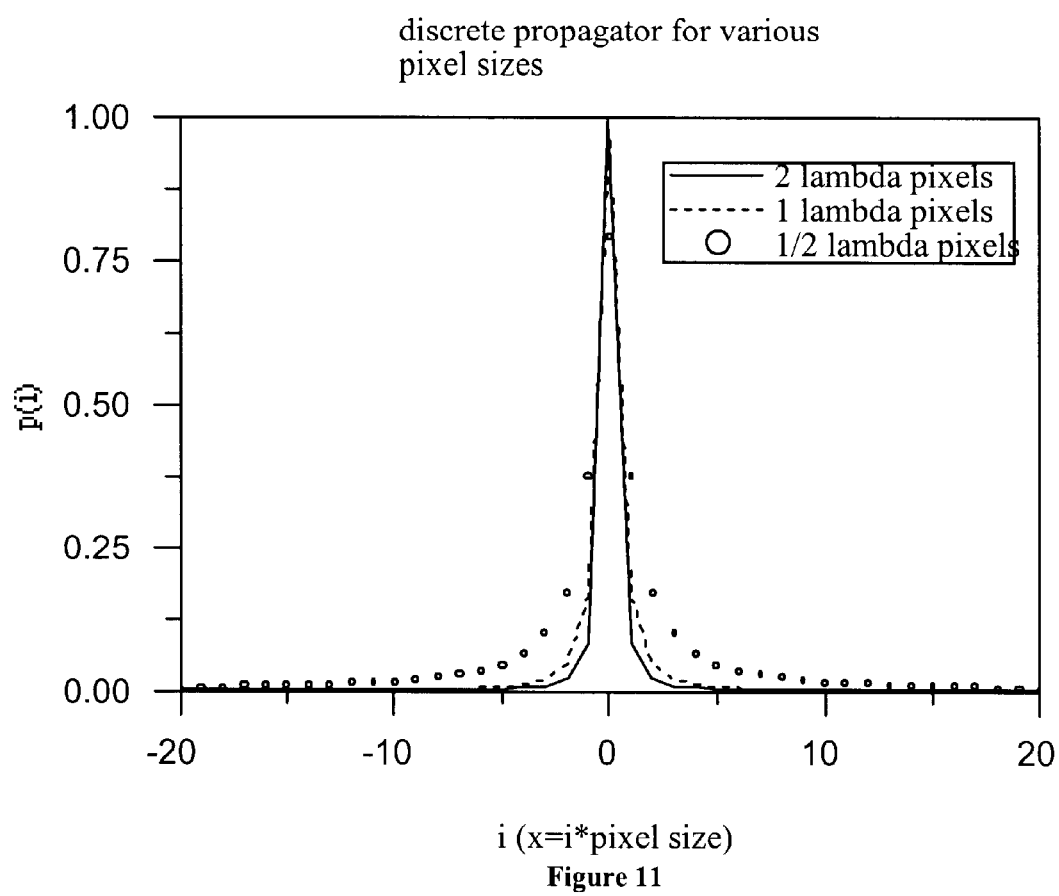
FIG. 11 shows the discrete propagator for $\Delta=2\lambda$, $\Delta=\lambda$ and $\Delta=\lambda/2$ for the new 'big pixel' parabolic method.

A slight vacuum can be applied to the tube to make a tighter fit as needed for the latex version. This shield is disposable and contributes to the esthetics and sanitation of the scanner. A tilting cot provides a comfortable means in patient positioning, shown in FIG. 2. The patient stands on the foot rest when the cot is vertical. Then the cot tilts to the horizontal position for the scanning process. The breast is then pendant in the water bath tank. One breast at a time is scanned. The tilt process is reversed for patient exit.

Some of the important specifications for the scanner are given in TABLE 2.1 below. Said table illustrates the performance of both reflection tomography and inverse scattering transmission tomography. The in-plane and normal to plane spatial resolution of reflection tomography will approach 0.2 mm and 2 to 3 mm respectively (the vertical resolution may be increased to 1 to 1.5 mm with special apodizing functions).

The number of views for reflection tomography will be taken to be the number of depth resolution lengths per circumference of a circle of diameter equal to the lateral resolution of a single view. Thus, $N=\lambda[2R/A]/[c/(2Pf)]=4\lambda RPf/[cA]=4RP/A$ where $\lambda$ is wavelength, R is range to target from array, A is the active lateral aperture of the array, c is the speed of sound, P is the fractional bandwidth, and f is the center frequency of the signal. The total collection time for one slice is 12 seconds.

The in-plane spatial resolution of inverse scattering can be varied by choice of pixel size (this ability is not possible with reflection tomography and one of the new developments we report). In TABLE 2.1 above we use 2 wavelength pixels (0.6 mm at 5 MHz) as an example.

The number of views for inverse scattering tomography will be taken to be the same as for diffraction tomography which is $N=\pi D/\lambda$. For inverse scattering this generalizes to $N=\pi D/p=667$ at 5 MHz for D=5 inches and for p=pixel size=2 wavelengths. The frequency separation to replace the view-to-view angle separation for a complete high quality image reconstruction is given by $\Delta f=2\pi f/N==2\pi f/[\pi D/p]=2pf/D=0.047$ MHz. Using many views at one frequency is equivalent to using fewer views with more frequencies per view. This creates a speed up factor in data collection since many frequencies can be collected at each view in the same times would a single frequency. The frequency band for 16 frequencies is 0.047 MHz×16=0.752 MHz and requires only 667/16=42 views. For this example of p=2 wavelengths, the spatial resolution is 0.6 mm. If p=1 wavelength were used, then the spatial resolution would be 0.3 mm. The total single slice, data collection time for 42 views and 16 frequencies is 4.3 seconds.

The block diagram of the scanner electronics is shown in FIGS. 3a–3b. Starting on the left, the transducer array is 8 by 96 elements. Each row has a receiver multiplexer (MUX) that feeds one of 8 analog to digital converters (ADC). Two ADCs are packaged on one GaGe™, Montreal, QC, Canada, "CompuScope 12100™" card and is clocked at 30 million samples per second (www.gageapplied.com). Each of the 8 channels digitizes 6,000 samples simultaneously per transmit event. Each transmit event is a transmission from a single element or from a single column (or part of a column). Also shown is a potential future expansion (using even and odd columns to separate MUXs) where 4 more GaGe cards are added to each Pentium-III computer or to 4 additional separate computers. If the PCI bus in each computer runs at 100 Mbytes/sec then each channel on the GaGe card runs at 25 sample/micro-sec (two Bytes/sample) into the PCI bus. Then 6000 samples will be transferred in 6000/25=240 microseconds on a single channel. This closely matches the 30 samples/micro-sec digitization rate. The computational load is can be handled is several ways: (1) array processor boards; (2) Apple G4 computers with their velocity engine that when programmed properly and matched to compatible problems, operates up to 4 GFLOPS (4 billion floating operations per second); or (3) by parallel computers. Our first choice would be to place one dual G4 PCI card in one slot each of the 4 computers. This would provide 4×2=8 G4 computers, which would provide a maximum of 32 GFLOPS. We could also put two G4 cards in each computer for a maximum of 64 GFLOPS.

TABLE 2.1

| Scanner Specifications | | | |
|---|---|---|---|
| Diameter of water bath tank | 9 inches | Depth of water bath tank | 13 inches |
| Water temperature stability | ±0.1 degrees F. | Ground fault and safety protection | yes |
| Patient hand controlled interrupt | Yes | Breast stabilizing disposable liner | yes |
| Antibacterial water in tank | Yes | Disposable sanitary liners per patient | yes |
| Inter array separation | 5 ± 2 inches | | |
| Center frequency of arrays | 5 MHz | Percent bandwidth of arrays | 70 percent |
| Size of each array (elements) | 8 by 96 | Waterproof cable built in | yes |
| Number of sub cables/array | 768 | Impedance of sub cable (Ohms) | 50 |
| Length of arrays | 4.91 inches | Height of arrays | 0.736 inches |
| Vert. rotation of arrays | 370 degrees | Vert. motion of arrays | 6 inches |
| Tilt of arrays | 0 ± 30 degrees | Arrays identical | yes |
| Center lateral resolution/view, r = 3" | 1.47 mm | | |
| Collection time per reflection view | .34 sec | # views for reflection tomography | 19 to 36 |
| | | Total collect time for reflection slice | 12 sec |
| Spatial resolution for reflect tomog | 0.2 mm planar 2–3 mm vert. | Contrast resolution: reflect tomog | 15 to 1 |
| Number of reflection vertical slices | up to 153 | | |
| Collect time for inverse scat view | 0.102 sec | # views for inverse scat tomogra'y | 667 @ 1 freq 42 @ 16 freq |
| | | Total collect time/slice for inv. scat | 68 sec @ 1 freq 4.3 sec @ 16 freq |
| Spatial resolution: Inv. Scat. tomog | 0.3–0.6 mm pln 2–3 mm vert | Contrast resol'n: Inv. Scat. tomog | 100 to 1 |
| Frequency separation to replace angle separation for 667 views | 47 kHz | Frequency band = 16 × 47 kHz = | 752 kHz |
| Number of inv scat. vertical slices | up to 153 | | |

The question of loading the PCI bus has been examined and is not a problem since our algorithms are course grained and each grain (part) needs minimum communication with the other grains. Thus similar operations can run in parallel on all the G4s and parts of each G4 (each G4 has 4 parallel SIMD processors). SIMD (single instruction multiple data) computers also work well with our course grained algorithms. The natural grain divisions are frequency, view angle and slice height.

The signals to the transmitter elements are formed by an arbitrary wave form generator card (such as the GaGe™ CompuGen 1100) that is placed in the PCI bus of one of the computers that acts as the master computer. It synchronizes the actions of the other computers; this is not a time consuming task since each computer is largely independent. The output of the waveform generator is amplified by a linear amplifier and sent to the transmitter MUX. The MUX will be designed to allow future expansion for using 2 to 8 linear amplifiers to be placed after respectively 2 to 8 delay lines(connected to the common wave form generator) to form transmit beams. The MUX circuits will be solid state analog switches of either the diode network type or of the Supertex™ (Sunnyvale, Calif. 94089) MOS (metal oxide semiconductor) type. We have used the diode network type with success in our present scanner (HYMEUS). The diode network requires more printed circuit (PC) board space, but has lower series resistance (about 5 Ohms) and low shunt capacitance. The Supertex approach uses less PC board space (the HV20822 has 16 switches in a 0.354 inch square package) but has higher series resistance (about 25 Ohms) and shunt capacitance (20 pf off, 50 pf on).

The diode network is a safe bet. However, we will look at placing the Supertex switches in a the MUX circuit bays close to the arrays to reduce cable capacitance and to use preamplifiers or buffer amplifiers after the Supertex switches to reduce the effect of their higher resistance and capacitance. The Supertex is not a bad choice and is used in many commercial ultrasound scanners with normal cable lengths from probe to chassis where space-savings is important in the chassis. The MUX circuits will use two stages, both for the transmitter and receiver connections.

The tank and scan motion control will be constructed and assembled as per well known methods and components known to the art. The arrays can be built by transducer jobbers such as Blatek, State College, Penn. The engineering and tooling for the arrays has already been completed; and allow the present array we are using (8 rows and 16 columns) to be replicated 6 times per new array (to make a 96 by 8 element array).

A more detailed understanding of a suitable MUX shown in FIG. 3a is given in FIG. 3b. The MUX circuit is divided into two natural parts, the transmitter MUX and the receiver MUX. The transmitter MUX is shown in the top part of FIG. 3b. The transmitter portion consists of programmable arbitrary waveform generator, a power amplifier, a protection circuit (which blocks the signal if the voltage exceeds a critical threshold), and a programmable gain module can provide independent gains to each of 8 separate output lines. The 8 independent output lines drive respective 8 independent rows of the 96 column transducer. Each row has six multiplexers, labeled A through F, that multiplex to 16 respective elements on that row, so that 6×16=96 elements per row. Each of the said six multiplexers drives one row of an 8 row by 16 column sub0array. The 6×8=48 multiplexers labeled S1A through S8A for column A through SiF through S8F for column F are 16 to 1 supertex MOS, analog, high voltage switches.

The receiver multiplexer is shown in the bottom half of FIG. 3b and consists of two subsections. The first subsection consists of six modules that multiplex 128 to 16. This is accomplished by 16 daughter cards that each multiplex 8 to I using divide gates, where note that 8×16=128 inputs; each subarray has 8 rows and 16 column=128 elements to match. The outputs of the six modules in the first subsection then are routed to a matrix switch that selects which of 16 outputs of each module are connected to either 8 or 16 analog to digital converters. The matrix switch has 2×6×16 nodes that thus allows either 8 or 16 ADC to be used. The node switch can be diode switches or selectable preamps. (outputs can be parallel when deselected without loading the input to any ADC channel.

The design and construction of needed multiplexer circuit boards is a process well known in the art. We have experience in designing such multiplexers for the compression plate inverse scattering scanner and other scanners in our lab.

The circuit board fabrication can be sent to a jobber. The circuit boards layout work can be done by the Orcad software. The design and coding of the software for data acquisition is a well known process in the art. One can use the Labview™ application software from National Instruments™ (Austin, Tex. 78759-3504) for the main program to allow the use of a virtual instrument panel (showing scanner array position, digitized waveforms, gain settings, etc.). The inner loops of the Labview program will be written in C or C++ for speed. Algorithm implementation and programming may be done in Fortran or C or C++.

Reflection Tomogaphy and Inverse Scattering Imaging Algorithms

The algorithms used for reflection tomography are given in the report section of this proposal. The exact algorithms for inverse scattering are given by Borup et al in [D. T. Borup, S. A. Johnson, W. W. Kim, and M. J. Berggren, "Nonperturbative diffraction tomography via Gauss-Newton iteration applied to the scattering integral equation," *Ultrasonic Imaging* 14, 69–85, (1992).]. We show here a faster version of inverse scattering that uses forward propagating wave solutions. This method is an approximate method that is much more accurate than the Born or Rytov methods, and even approaches closely the accuracy of the exact solution. An outline of the theory will be given here, but a full account of several approaches using this method may be found in the literature and our patent.

We start with the Hehnholtz wave equation $(\partial^2/\partial x^2 + [k^2(x,y)\partial^2/\partial y^2])f(x,y)$. Next we take the Fourier transform with respect to y and then factor the resultant equation. Note that the convolution theorem of Fourier transforms is used, where * is convolution. Let $f(x, \lambda)$ be Fourier transform of $f(x, y)$ with respect to y. The result is:

$$\left(\frac{\partial}{\partial x} + i\sqrt{\frac{1}{2\pi}(\hat{k}^2(\lambda))^* - \lambda^2}\right)\left(\frac{\partial}{\partial x} - i\sqrt{\frac{1}{2\pi}(\hat{k}^2(\lambda))^* - \lambda^2}\right)\tilde{f}(x,\lambda) = 0.$$

We next note that the factors represent wave moving to the left and to the right along the x axis. Taking only the wave moving from left to right and we have an operator only in $\partial/\partial x$ and a square root operating on $f(x, \lambda)$. It is a parabolic equation. Solving the differential equation for $f(x, \lambda)$) and taking the inverse Fourier transform with respect to $\lambda$ gives $$f(x, y) = \frac{1}{2\pi}\int_{-\infty}^{\infty} \tilde{f}(x_0, \lambda)e^{-i(x-x_0)\sqrt{k^2-\lambda^2}} e^{i\lambda y}d\lambda, \quad x > x_0 > 0.$$

This formula is the basis for a multitude of marching approaches for solving the direct scattering problem. The general idea is to perform the integral on a line parallel to the y-axis and to propagate the angular spectra forward by an increment of x. Then the process is repeated for additional increments of x. The method of dealing with the square root varies between methods (including a binomial expansion). Our approach follows this general pattern but adds additional refinements to improve accuracy and speed. This completes the outline of the parabolic method.

The parabolic method has allowed us to design the proposed scanner to use inverse scattering at 5 MHz. Using several tricks has accomplished this. One trick is to use larger pixels to reduce the computational load. Other tricks involve further approximations the increase speed but not performance.

The basis of inverse scattering imaging is to solve by optimization methods the following lest squares problem for the vector of independent variables γ, whose components are the image parameters. Let $f^{(measured)}(x_{det})$ be the measured field on detectors and let $f^{(scat)}(x_{det})$ be the direct scattering modeled field as a function of γ and the incident field $f^{(inc)}(x)$ in the body and on the detectors. Then $f^{(inc)}(x)=f^{(inc)}(x;\gamma, f^{(inc)}(x))$. Then the scattering potential I=is found by finding the minimum value of the norm of the measurement residual R, where, R is defined as the difference of the square of the Euclidean distance, in Hilbert space, between the measured and computed fields on the detector. This formula is the basis for a multitude of marching approaches for solving the direct scattering problem. The general idea is to perform the integral on a line parallel to the y-axis and to propagate the angular spectra forward by an increment of x. Then the process is repeated for additional increments of x. The method of dealing with the square root varies between methods (including a binomial expansion). Our approach follows this general pattern but adds additional refinements to improve accuracy and speed. This completes the outline of the parabolic method.

The parabolic method has allowed us to design the proposed scanner to use inverse scattering at 5 MHz. Using several tricks has accomplished this. One trick is to use larger pixels to reduce the computational load. Other tricks involve further approximations the increase speed but not performance.

The basis of inverse scattering imaging is to solve by optimization methods the following lest squares problem for the vector of independent variables γ, whose components are the image parameters. Let $f^{(measured)}(x_{det})$ be the measured field on detectors and let $f^{(scat)}(x_{det})$ be the—direct scattering modeled field as a function of γ and the incident field $f^{(inc)}(x)$ in the body and on the detectors. Then $f^{(inc)}(x)=f^{(inc)}(x;\gamma, f^{(inc)}(x))$. Then the scattering potential I=is found by finding the minimum value of the norm of the measurement residual R, where, R is defined as the difference of the square of the Euclidean distance, in Hilbert space, between the measured and computed fields on the detector.

$$\text{Min}_\gamma \|f^{(measured)}(x_{det})-f^{(inc)}(x_{det};\gamma,f^{(inc)}(x))\|^2 \equiv \text{Min}_\gamma \|R\|^2$$

We have shown how this optimization problem may be solved by Gauss Newton, Fletcher Reeves, Riebier Polak and other methods [D. T. Borup, S. A. Johnson, W. W. Kim, and M. J. Berggren, "Nonperturbative diffraction tomography via Gauss-Newton iteration applied to the scattering integral equation," *Ultrasonic Imaging* 14, 69–85, (1992). APPARATUS AND METHOD FOR IMAGING WITH WAVEFIELDS USING INVERSE SCATTERING TECHNIQUES, S. A. JOHNSON ET AL.], herein included as reference. Formerly we used integral equations and finite difference time domain (FDTD) methods to solve the forward problem. Suppose we use the integral equation form of the wave equation for the scattering in the body. This is given by $f(x)=f^{(inc)}(x)+k^2_o \int G(k_o,x-y)\gamma(y)f(y)d^Qy$, where G is the Green's function and Q is the spatial dimension of the problem, which after discretization can be written in matrix notation as $f=f^{(inc)}+G[\gamma\backslash]f$. The field in the body can be solved as $f=(I-G[\gamma\backslash])^{-1}f^{(inc)}$. The field on the detector is $f(x)=f^{(inc)}(x)+k^2_o \int G(k_o,x-y)\gamma(y)f(y)$, which when discretized is $f^{(det)}=f^{(inc,\ det)}+TG[\gamma\backslash]f$, where T is an operator that limits or truncates the field to the detector and $[\gamma\backslash]$ is a diagonal matrix. On substitution of the internal field into the detected field equations we have $f^{(det)}=f^{(inc,\ det)}+TG[\gamma\backslash](I-G[\gamma\backslash])^{-1}f^{(inc)}$. The Jacobian is defined as $J=\partial f^{(det)}/\partial[\gamma\backslash]$. The solution $[\gamma\backslash]$ is found by the two coupled iteration formulas $\gamma^{(n+1)}=\gamma^{(n)}+(\delta\gamma)^{(n+1)}$, where δγ is solution of linear problem $J^{(n)}(\delta[\gamma\backslash])^{(n)}=-R^{(n)}$.

The method of minimizing the norm of the residual using the Parabolic Jacobian is more complicated but follows the same principles. The derivation and use of the Parabolic Jacobian is based on a recursion process and is found in our patent [APPARATUS AND METHOD FOR IMAGING WITH WAVEFIELDS USING INVERSE SCATTERING TECHNIQUES, S. A.JOHNSON ET AL.] in a subsection called "Inverse problem and construction of Jacobian" in section call "EXAMPLE 12, PARABOLIC MARCHING METHODS".

We form a Jacobian for the parabolic method, as for example with integral equation methods, and incorporate it as part of the above iterative formulas. We next show how the new parabolic method performs in terms of speed and accuracy by simulating the geometry and parameters for similar scanners and the proposed scanner shown in FIGS. 4a–7c.

EXAMPLES OF EMBODIMENT OF INVENTION

Example 1

This example is a compression plate ultrasound scanner combining both reflection imaging and transmission inverse scattering imaging. This is not the geometry for the water bath scanner, yet we see that both geometries can produce images of sound speed and attenuation.

We specify two arrays facing each other, with their faces mutually parallel. Each array can be a 1-D array or a 2-D array of transducer elements. We have constructed compression plate scanner where each array is a 1-D array with 256 elements with ½ element separation at 2 MHz. A drawing of this compression plate configuration is shown in FIGS. 4a and 4b. Therein is shown the side view of breast between two compression plates and showing end view of the top and bottom linear array transducers and their translation motions. The two opposing transducers allow transmission data to be collected that includes scattering and diffraction into wide angles and thus improves spatial resolution. The motion of the top and bottom linear 1-D array or 2-D array is shown to image successive vertical slices of the breast. The top and bottom compression plates are also shown.

The array geometry can be extended to provide improved imaging by adding side reflecting plates or side transducer arrays which also serve as side compression plates. This extension in function is shown in FIGS. 4c and 4d. In particular, FIG. 2.4c shows an isometric view of compression plate showing options for placing transducer elements either inside of outside of the top and bottom compression plates. We also note that the top and bottom transducer array can be used for reflection imaging as well. The side plates with transducers may also be used for reflection imaging.

FIG. 4d Shows an isometric view of compression plate showing options for placing side compression plates with optional transducer elements either inside of outside of the side compression plates. A front compression plate and optional reflector or transducer array can also be added as a front plate as is shown in FIG. 4e.

The bandwidth for the reflection imaging mode is determined by a Blackmann window from 0 to 2 MHz with a center frequency of 1 MHz. The reflection mode beam former uses a 16 element segment of the array to create a beam perpendicular to the array face which is then translated across the array. The beam former is focused at all ranges for both the transmitter and receiver elements and a Hamming window is used to apodize both the transmitter and receiver beams. The data is generated with the generalized born approximation corrected for time delay and attenuation loss through the tissue. The generalized born scattering model and image arrays are 512 by 200 with a ¼ at 2 MHz pixel size. The reflection image is made by software that simulates a reflection mode scanner. Notice that the speckle caused by the random component prevents the identification of the targets (except possible the cyst although there are speckle artifacts at least as bright).

The inverse scattering data is generated by computer simulating using a direct scattering solver. This solver generates data at all elements on the receiving array for each element transmitting on the opposite transmitter array. The inverse scattering image is formed by software the inverts this simulated data. Perfectly reflecting plates (infinite impedance) are assumed to exist on the other two sides. Two frequencies, 1 MHz and 2 MHz, are used. The image array is 256 by 100, ½ at 2 MHz, pixels. For 30 iteration, the algorithm requires 1.5 hr. of CPU time on a 400 MHz Pentium II. The model defined in FIGS. 1–2 was used to generate data which was then inverted with the parabolic algorithm.

The tissue model comprises five tissue speeds of sound and attenuations and was created with the following tissue parameters: For speed of sound: $C_{fat}$=1458 m/s, $C_{parenchyma}$=1519 m/s, $C_{tumor}$=1564 m/s, $C_{cyst}$=1568 m/s, $C_{skin}$=1525 m/s, For attenuation: $a_{fat}$=0.41 dB/cm/MHz, $a_{parenchyma}$=0.81 dB/cm/MHz, $a_{tumor}$=1.18 dB/cm/MHz, $a_{cyst}$=0.10 dB/cm/MHz, $a_{skin}$=0.81 dB/cm/MHz. A value of 1500 m/s for water was assumed. A random component (with mean 0 and uniformly distributed from −50% to +50% of the average speed of sound) was added to the speed of sound model. The reflection model is generated from this random component as if real tissue (where impedance Z fluctuations would create the scattering; however we assume constant density r, the result is the same since Z=rC). The performance of the standard parabolic method with 1.2 wave length pixels is shown if FIGS. 5a through 5d.

FIG. 5a. Shows the speed of sound model of a breast compressed between two plates as in a mammogram. The values range from 1438 m/s (black) to 1602 m/s (white). The scattered waves were then simulated for sources and receivers only on the top and bottom of the image. Note the built in sound speed fluctuation; this is intentional and is not noise.

FIG. 5b shows the reconstructed image of sound speed (including fluctuations) using a ½ wavelength pixel parabolic inverse scattering algorithim. Values range from 1419 m/s (black) to 1602 m/s (white). All targets are visible. If sources & receivers are added to the sides, the reconstructed image becomes almost identical to original. Note the reproduced fluctuation; this is truth and not noise.

FIG. 5c. Shows the corresponding attenuation model. The values range from 0.0 dB/cm/MHz (black) to 1.202 dB/cm/MHz (white). Note that no fluctuations are added to attenuation for this simulation.

FIG. 5d. Shows the reconstructed image of the acoustic attenuation using a ½ wavelength pixel parabolic inverse scattering algorithm. Notice that all of the targets are clearly visible. If sources and receiver are added to the ends (sides) the reconstructed image becomes almost identical to original.

FIG. 5e. B-scan image created from simulated data for model defined in FIGS. 1–2 with scattering from fluctuation in speed of sound. The image range is −50 dB (black) to 0 dB (white). The bandwidth was 2 MHz. Notice greater noise and speckle here than in FIGS. 4a–4c.

Conclusion for Example 1

The original parabolic method used $\lambda/2$ pixels. With $2\lambda$ pixels, there are 4×4=16 times less pixels, 4 times fewer views and 4 times the inner loop speed, for a factor of $4^4$=256. Changing integral equations from $\lambda/4$ to $2\lambda$ pixels, the speed up is 8×8 less pixels and 8 time fewer views (the inner loop does not change significantly) for a factor of $8^3$=512. But the old $\lambda/2$ parabolic is 500 time faster than the ¼ integral equation algorithm; the new parabolic wins. At 5 MHz the $2\lambda$ pixel spatial resolution is 0.6 mm. With the new parabolic method two options still exist: (1) use $\lambda/2$ or $\lambda$ pixels and run the imaging program over night for those slices that are wanted at 0.3 mm spatial resolution; or (2) increase computing power. By Moore's law, computing speed increases 2.5 times per 2 years, so in about 12 years 0.3 mm resolution will be standard.

Example 2

Inverse scattering images from real lab data from two ¼ inch, 5 Hz Panametrics™ video scan transducers facing each other and using parabolic wave equation.

This example illustrates that our break through in large pixel parabolic codes is practical. We applied it to existing time of flight data (digitized waveforms) that was collected to be analyzed by time of flight tomography (a modified x-ray CT algorithm). No transducer array was used as a receiver (thus no diffraction pattern was recorded), only opposite facing ¼ inch piston transducers (only one receiving transducer fixed relative to transmitting transducer). Nevertheless, the parabolic inverse scattering method has defined the two holes in an agar phantom somewhat better than the straight line time of flight method (see FIGS. 6a–6b).

FIG. 6a. shows the "time of flight image" i.e., speed of sound map (image) obtained from real time of flight data collected on laboratory scanner through application of a time of flight CT algorithm. Minimum=black=1477 m/s, Maximum =white=1560 m/s.

FIG. 6b Shows the sound speed map (image) obtained after 15 steps of new fast 2 wavelength pixel algorithm starting with the same real lab data as used by time of flight CT algorithm. Minimum=black=1465 m/s, Maximum= white=1560 m/s. Although the data used was not designed for this new algorithm, yet the image is better than the corresponding "time of flight image". Based on this evidence we therefore point out that with hardware designed to be compatible with and optimized for this new method, we rapidly compute images of speed of sound at 5 MHz that exceed the spatial resolution of time of flight images by a factor of 10 (0.6 mm vs. 6 mm). With further effort we can obtain images of 0.3 mm and even 0.15 mm (by combining reflection and transmission data). We have tested this claim with computer simulation and the results support the claim as we show in FIGS. 7a–8c in the next example.

Conclusion for Example 2

The new fast algorithm has been tested in adverse conditions with poor data from the laboratory (real data!) and performs better than the "gold standard" time of flight CT algorithm. Its predicted performance should be about 10 timers better when using data that is designed to meet it's computational and interface requirements. This will be verified in the next two examples.

Example 3

Inverse scattering images from simulated data from ¼ inch Pamametrics video scan transducers using parabolic wave equation.

For this computer simulation example we use the following parameters: Frequency=5 MHz. Number of frequencies=1. Pixel dimension=21 Image size 100 by 100 pixels=2.36 by 2.36 inches. Element aperture=0.236 inches. 90 element translation positions for 90 view angles. Speed of sound values (m/s): cwater=1500, cskin=1505, cfat=1490, cparenchyma=1505, ctumor=1510. The image size can easily be doubled or beyond for real data, The results of this simulation are shown in FIGS. 7a and 7b. FIG. 7a shows the normalized true speed of sound image, $[c_o/c\,(x,y)-1]$, used to generate simulated data.—FIG. 7b shows the normalized image, $[c_o/c(x,y)-1]$, reconstructed by the 2 wavelength pixel algorithm.

Conclusion for Example 3

Using an accurate model of the two, 5 MHz, ¼ inch diameter piston transducers rather than lab data that was not design ed with the transducers accurately aligned and calibrated, the spatial resolution is about 4 times better than the lab data. In fact, the images are remarkable. This simulation experiment suggest a follow up simulation experiment where a much larger receiver aperture is used to sample a much greater part of the scattered (diffracted) waves in the forward direction. In this case an additional factor of improvement should be obtained. This experiment is performed in the next example.

Example 4

Images made from simulated data for the same phantom as in EXAMPLE 3, but with the ¼ inch diameter piston transducer replace with an transducer array of 120 elements, each 2 wavelength in width and separation.

See FIGS. 8a–8c for the comparison of the time of fight image using CT algorithm with straight acoustic rays vs. the new, high speed inverse scattering method with ½ (two wavelength) size square pixels. The phantom for generating computer simulated data (used by the inversion algorithm in FIGS. 7a–8c) are the same, but the transducers are different (FIGS. 7a–8c uses piston transducer, while FIGS. 8a–8c uses a 120 element array). $c_0$=1500 m/s. The parameters used in FIGS. 8a–8c are: D=pixel size=2 1 at 5 MHz=0.6 mm; Numeric array size=180 by 120 pixels=10.8 by 7.2 cm=4.25 by 2.84 in; outside circle diameter=6 cm=2.36 in; the receivers are located at 151 points centered on the 180 pixel border; the left and right hand sides of the 180 by 120 array are assumed to be perfectly reflecting (infinite impedance) boundaries; 120 views, 2 frequencies at 2.5 MHz and 5 MHz; cfat=1485; cparen=1515; ctumor=1520; ccyst=1520; and cskin=1515.

FIG. 8a shows a 120 by 120 pixel image of Re(g) for the true object. FIG. 8b shows a 120 by 120 pixel image of the Re(g) reconstructed using the straight line, time of flight CT algorithm. FIG. 8c shows a 120 by 120 pixel image by new fast parabolic algorithm. Iteration 40, time=22 min. Note big improvement over CT method.

Note the greater accuracy of the image from new algorithm (right) vs. the time of flight image (center). Also not that using an array (FIG. 8c) produces a much better image than a single piston receiver (FIG. 7b).

Conclusion for Example 4

Increasing the receiver aperture does indeed improve spatial resolution as predicted by theory. The new algorithm is stable, accurate and fast and can use this increased data set size. The results of the four (4) Examples are self consistent and a speed up factor of 256 over previous parabolic methods is true.

Transition to 3-D imaging

The transition from 2-D algorithms (either standard parabolic or fast multi pixel parabolic) is straight forward and only involves replacing the 1-D convolution kernel by a 2-D convolution kernel and other obvious dimension al changes. We have programmed a standard parabolic algorithm to make 3-D inverse scattering images. The image was 150 by 150 in each (x,y) topographic plane with 60 stacked planes (z axis direction). FIGS. 9a and 9b show the results of this simulation.

FIG. 9a shows the 3-D breast model with the true speed on sound on a z-y plane at y=75. In particular the image is given by: speed of sound c(x, 75, z); positive contrast=4.6%; negative contrast=5.4%; gray scale limits are max black=−6% and max white=8%. Note that the three simulated tumors near the center are spatially resolved and reconstructed accurately.

We conclude from these images that 3-D imaging is a straight forward modification of 2-D imaging.

Value of incortporating reflectivity imaging by reflection tomography

We show next that incorporating reflection tomography imaging with the inverse scattering algorithm is straightforward and valuable. The speed of sound image made by inverse scattering can be used with ray tracing (either straight ray approximation or actual ray tracing) to form a correction map or correction table to adjust the delay times for back propagation of data from the a common transmission and reception transducer array. This process is well known to the art. The main difficulty to date has been the obtaining of an accurate speed of sound image to proceed with the mapping process to generate the correction table. The inverse scattering method fills this requirement almost pefectly. We show the result of straight line ray tracing through a speed of sound image, made by time of flight tomography, to correct a reflection tomography image of human breast tissue in a thin plastic cylinder.

FIG. 10a show an image made with a commercial B-scan Image of the cancerous breast tissue in the cylinder. A 3.5 MHz ultrasound sector probe was used while the phantom was submerged under water. The commercial scanner used 32 beam former channels.

FIG. 7b shows a reconstructed image made by reflection tomography of same breast tissue sample at approximately the same level. Made with a Water Bath, Reflection Tomography scanner at 5 MHz. This image was reconstructed from 12 vertical source/receiver pairs on a 420×420 grid using 0.25 mm wide pixels. Corrections in time delays were made for speed of sound variations (but not for refraction effects). It takes approximately 1.5 hr. of CPU time to compute this image on a 27 MFLOP computer. The breast is encapsulated in a plastic container whose walls are clearly visible and the bright spots on the walls are four marker strings. The greatly improved quality of the reflection tomography image is obvious.

INVENTION DISCLOSURES FOR THE PARABOLIC INVERSE SCATTERING ALGORITHM—Large ($\Delta=2\lambda$) Pixels In our original parabolic disclosure: example 12 of APPARATUS AND METHOD FOR IMAGING WITH WAVEFIELDS USING INVERSE SCATTERING TECHNIQUES, S. A. JOHNSON ET AL., the forward propagation of the wavefield from f(x,y) to f(x,y+Δ) was performed by Fourier transforms via:

$$f(x,y+\Delta) = F_{\lambda \to x}^{-1}\{p(\lambda) F_{x' \to \lambda}\{f(x',y)\}\} \quad 1.1$$

where F and $F^{-1}$ denote the forward and inverse Fourier transforms and the exact propagator, p, is given by:

$$p(\lambda) = e^{-i\Delta\sqrt{k_0^2 - \lambda^2}} \quad 1.2$$

This propagation is exact. By the convolution theorem, 1.1 can be rewritten as:

$$f(x,y+\Delta) = \int f(x',y) p(x-x') dx' \quad 1.3$$

where $$p(x) = F_{\lambda \to x}^{-1}\{p(\lambda)\} \quad 1.4$$

In other words, the propagator can be implemented by convolution. The question is, for a discrete version of these equations, which is faster, FFT's and multiplication in the frequency domain or convolution in the spatial domain? FIG. 101 shows our discrete propagator, p(iΔ), for 3 cases: Δ=2λ, Δ=λ and Δ=λ/2 where λ is the wavelength.

Notice that for Δ=λ/2, if we assume that we can cut off the propagator at i=±20 then the implementation of the propagator by a direct convolution sum would require N*41 operations. This convolution length is probably too long to be any faster than the FFT implementation. However, the Δ=λ case can be cut off at i=±6 and the Δ=2λ case can be cut off at i=±3. In particular, we have found that the Δ=2λ case can be implemented with a cut off at i=±3 with no discernible error over the FFT implementation providing that the propagator is multiplied by a Blackmann window: p̂(i)=p(i) (0.42+0.5 cos(πi/(nfilt+1)) +0.08 cos(2πi/(nfilt+1))), i=−nfilt, . . . , nfilt where nfilt=3 for the Δ=2λ case. Without this filter multiplication, the parabolic propagation was found to be unstable. Apparently, even though the neglected values are small, simple truncation of the propagator results in at least one eigenvalue slightly greater than 1 resulting in exponential growth for large numbers of parabolic steps.

We had originally thought that the parabolic algorithm required Δ≦λ/2 in order to maintain accuracy for scattering from biological tissue contrasts. This is certainly true if one requires scattering at angles out to 45 deg. from the incident field propagation direction. However, for the computation of the all scattering in a ±15 deg. cone, Δ=2λ sampling is sufficient. Of course, in a typical medical imaging problem, there will be scattering at large angles, however, suppose that the receivers are 2λ segments. Then the receivers do not see this large angle scattering energy anyway. Thus, the Δ=2λ algorithm will accurately compute the received data. Since the pixel size is now larger, the number of views needed for a complete dataset is also reduced by a factor of 4 over the Δ=λ/2 algorithm.

Compared with the previous Δ=λ/2 algorithm, the speedup in compute time is given by: 4 times fewer views * 16 times fewer pixels*speedup factor of short convolution vs. FFT propagator.

Even assuming that the short convolution buys only a factor of 4 over the FFT (it is likely better than this for nfilt=3), the algorithm is still 256 times faster than the previous algorithm for the same sized object at the same frequency.

Pseudo code definitions of the plane wave parabolic algorithms for the frequency domain Parameter definitions $c_0$=background medium speed of sound in m/s

* denotes the complex conjugate $\|x\| = x \; x^*$ $\|array\|^2 = \Sigma_{i,j \ldots} \|array(i,j, \ldots )\|^2$ where i,j, . . . are the indices of the array <array1,array2>=$\Sigma_{i,j \ldots}$ array1(i,j, . . . )* array2(i,j, . . . )

x̂ denotes discrete convolution

Δ=pixel dimension nx=x-axis array dimension (x is normal to the parabolic propagation direction)

ny=y-axis array dimension (y is parallel to the parabolic propagation direction)

nr=the number of receivers per view nv=the number of plane wave views from 0 to 360 deg.

nf=the number of frequencies used nfilt defines the width of the short convolution propagator: the values f(−nfilt+n) to f(n+nfilt) are used to propagate one step for field index f(n).

ne defines the number of samples used to define a receiver element. Each receiver is −ne to ne, Δ samples long. For a point receiver, ne is set equal to 0.

Propagator definition

The following pseudo code defines the short convolution propagator generation.

$\delta\mu = 2\pi/(nx\Delta)$ for lf=1, . . . ,nf
   for n=1, . . . ,nx
   λ=(n−1)δλ
   if n>nx/2, λ=(n−nx−1)δλ
   if λ<$k_0$(lf) then
     temp(n)=exp(−i Δ sqrt($k_0$(lf)$^2$−λ$^2$))
   else
     temp(n)=exp(−Δ sqrt(λ$^2$−$k_0$(lf)$^2$))
   endif
   next n
The next step is done by the FFT algorithm:
   for m=1,nx
   temp2(m)=0
   for n=1,nx
   temp2(m)=temp2(m)+temp(n) exp(i 2π(n−1)(m−1)/nx)/nx
   next n
   next m
   for n=0,nfilt
     wind=0.42+0.5 cos(πn/(nfilt+1))+0.08 cos(2πn/(nfilt+1))
     prop(n,lf)=temp2(n+1) wind
   next n
   for n=−nfilt,−1
     prop(n,lf)=prop(−n,lf)
   next n
   next lf The window (wind=Blackmann in the present case) applied above to the short convolution propagator is essential for stability.

Definition of the propagator operation
The notation:

temp→tempˆprop(.,lf) will henceforth be used to denote the following computation:
        for n=1, . . . ,nx
        temp2(n)=temp(n)
        next n
        for n=−nfilt+1,0
        temp2(n)=temp(1−n)
        next n
        for n=nx+1,nx+nfilt
        temp2(n)=temp(2nx−n+1)
        next n
        for m=1, . . . ,nx
        temp (m)=0
        for n=n−nfilt,n+nfilt
        temp(m)=temp (m)+temp2(n)prop(m−n,lf)
        next n
        next m Note that this implementation applies the boundary condition for an infinite impedance boundary (f=0) at the array ends 1 and nx.

Definition of the rotation operator
    The notation $$tr=Rot(t,\phi)$$

will henceforth denote the rotation of the function in array t(nx,ny) by $\phi$ radians followed by placement into array tr(nx,ny) via bilinear interpolation.

Definition of the receiver location array
    The nr receivers are located at the points mr(lr), lr=1, . . . ,nr where each mr(lr) is an element of [1+ne, . . . ,nx−ne]

Definition of the receiver sensitivity function
    Receiver lr is centered at point mr(lr) and extends from mr(lr)−ne to mr(lr)+ne. The array wr(−ne:ne,nf) is set to be the receiver sensitivity function on the support of the receiver for each frequency 1, . . . ,nf.

Code 1. Frequency domain, plane wave source, parabolic algorithm
common $k_0$,Δ,prop,wr,mr
common/gamma/γ
complex γ(nx,ny), grad(nx,ny), tg(nx,ny), p(nx,ny)
    f(nr,nv,nf), r(nr,nv,nf),tr(nr,nv,nf), wr(−ne:ne,nf), prop(−nfilt:nfilt,nf)
real $k_0$(nf),freq(nf)
integer mr(nr)
set Δ=pixel size in m.
set freq(lf), lf=1, . . . ,nf in Hz.
$k_0$(lf)=2π freq(lf)/$c_0$, lf=1, . . . ,nf
set the prop() array as described in "Definition of the propagator operation" section above.
set wr as described in "Definition of the receiver location array" section above.
set mr as described in "Definition of the receiver sensitivity function" section above.
select a residual termination tolerance $\epsilon_1$
select a gradient magnitude termination tolerance $\epsilon_2$
select a maximum number of iterations, nrp
read the data f(nr,nv,nf)
resdata=∥f∥
set γ equal to a starting guess
call scatter(γr)
r→r−f
res0=∥r∥/resdata
call jacobian_adjoint(r,grad)
$r_1$=∥grad∥$^2$
p→−grad
g0=∥grad∥
for lrp=1, . . . ,nrp
    call jacobian(p,tr)
    α=−Re{<r,tr>}/∥tr∥$^2$
    γ→γ+αp
    call scatter(γ,r)
    r→r−f
    res(lrp)=∥r∥/resdata
    call jacobian_adjoint(r,tg)
    g(lrp)=∥tg∥/g0
    if res(lrp)<$\epsilon_1$, go to line 100
    if g(lrp)<$\epsilon_2$, go to line 100
    β=Re{<tg,tg−grad>}/$r_1$
    if β<0,β→0
    $r_1$=∥tg∥$^2$
    p→−tg+βp
    grad→tg
next lrp
100 write γ to a datafile
stop
subroutine scatter(γ,f)
common $k_0$,Δ,prop,wr,mr
complex t(nx,ny),γ(nx,ny),temp(nx),f(nr,nv,n),wr(−ne:ne,nf),
    prop(−nfilt:nfilt,nf),tr(nx,ny)
real ko(nf)
integer mr(nr)
for lfr=1, . . . ,nf
t(n,m)=exp(−i $k_0$(lf)Δγ(n,m)), n=1, . . . ,nx, m=1, . . . ,ny
for lv=1, . . . ,nv
    $\phi$=2π(lv−1)/nv
    tr=Rot(t,$\phi$)
    temp(n)=1, n=1, . . . ,nx
    for m=1, . . . ,ny
        temp→tempˆprop(.,lf)
        temp(n)=temp(n) tr(n,m), n=1, . . . ,nx
    next m
    for lr=1, . . . ,nr
        f(lr,lv,lf)=0
        for le=−ne, . . . ,ne
            f(lr,lv,lf)=f(lr,lv,lf)+temp(mr(lr)+le)wr(le,lf)
        next le
    next lr
next lv
next lf
return
subroutine jacobian(δγ,δf)
common $k_0$,Δ,prop,wr,mr
common/gamma/γ
complex t(nx,ny),γ(nx,ny),temp(nx),wr(−ne:ne,nf),prop(−nfilt:nfilt,nf),tr(nx,ny)
    δt(nx,ny),δtr(nx,ny),temp2(nx),δf(nr,nv,nf)
real ko(nf)
integer mr(nr)
for lf=1, . . . ,nf
t(n,m)=exp(−i $k_0$(lf)Δγ(n,m)), n=1, . . . ,nx, m=1, . . . ,ny
coeff=−i $k_0$(lf)Δ
for lv=1, . . . ,nv
    $\phi$=2π(lv−1)/nv
    tr=Rot(t,$\phi$)
    δtr=Rot(δt,$\phi$)

```
temp(n)=1, n=1, . . . ,nx
temp2(n)=0, n=1, . . . ,nx
for m=1, . . . ,ny
   temp→tempx̂prop(.,lf)
   temp2→temp2x̂prop(.,lf)
   for n=1, . . . ,nx
      temp2(n)=(temp2(n)+temp(n) δtr(n,m) coeff) tr(n,m)
      temp(n)=temp(n) tr(n,m)
   next n
next m
for lr=1, . . . ,nr
   δf(lr,lv,lf)=0
   for le=-ne, . . . ,ne
      δf(lr,lv,lf)=δf(lr,lv,lf)+temp(mr(lr)+le)wr(le,lf)
   next le
next lr
next lv
next lf
return
subroutine jacobian_adjoint(δf,δγ)
common k₀,Δ,prop,wr,mr
common/gamma/γ
complex t(nx,ny),γ(nx,ny),temp(nx),wr(-ne:ne,nf),prop(-
   nflt:nfilt,ni),tr(nx,ny)
   δt(nx,ny),δtv(nx,ny),δtvr(nx,ny),δf(nr,nv,nf)
real ko(nf)
integer mr(nr)
δt(n,m)=0, n=1, . . . ,nx m=1, . . . ,ny
for lf=1, . . . ,nf
t(n,m)=exp(-i k₀(lf)Δγ(n,m)), n=1, . . . ,nx, m=1, . . . ,ny
coeff=-i k₀(lf)Δ
for lv=1, . . . ,nv
   φ=2π(lv-1)/nv
   tr=Rot(t,φ)
   temp(n)=1, n=1, . . . ,nx
   for m=1, . . . ,ny
      temp→tempx̂prop(.,lf)
      for n=1, . . . ,nx
         δtv(n,m)=temp(n)
         temp(n)=t emp(n) tr(n,m)
      next n
   next m
   temp(n)=0, n=1, . . . ,nx
   for lr=1, . . . ,nr
      for le=-ne, . . . ,ne
         temp(mr(lr)+le)=temp(mr(lr)+le)+δf*(lr,lv,lf)wr(le,lf)
      next le
   next lr
   for m=nx, . . . ,1
      for n=1, . . . ,nx
         δtv(n,m)=δtv(n,m)*temp(n)
         temp(n)=temp(n) tr(n,m)
      next n
      temp→tempx̂prop(.,lf)
   next m
   δtvr=Rot(δtv,-φ)
   δt(n,m)=δt(n,m)+δtvr(n,m) tr(n,m) coeff, n=1, . . . ,nx
      m=1, . . . ,ny
next lv
next lf
δt(n,m)=δt*(n,m), n=1, . . . ,nx m=1, . . . ,ny return
```

THE ENVELOPED TIME DOMAIN PARABOLIC ALGORITHM

The second invention disclosure for the parabolic inverse scattering algorithm is a means of avoiding local minima when imaging an object with many $\pi$ phase shifts and when starting from a zero (or a somewhat poor) initial guess. If one has only one frequency and the phase shift through the object is less than $\pi$ radians then one can converge to the global, correct solution from a starting guess of zero. If the phase shift is greater than $\pi$ then the algorithm will converge to a local minimum if a zero starting guess is used. Extrapolating this, if one has a bandwidth from fmin to fmax then convergence to the correct solution will occur from a zero starting guess only if the phase shift through the object is less than $\pi$ at fmin. For biological tissue at ultrasound frequencies, say 5 MHz, phase shifts of on the order of $10\pi$ are encountered. This means that fmin needs to be on the order of 1/10 th fmax. This is not possible with the typically 50% bandwidth transducers available at present.

In order to get around this difficulty, we have examined the use of starting guesses computed by straight line time of flight imaging. In this approach the time delay of the acoustic time pulse through the body is extracted from the data. Assuming that the energy took a straight line path through the body for each receiver (not a good assumption due to ray bending (refraction) and diffraction effects) then the speed of sound image can be reconstructed by well known x-ray CT type algorithms. We have found that these starting guesses will work up to a point but as we increase the size and contrast of the body up to that of tissue, we find that the time of flight image is not sufficiently close to the truth to allow inverse scatter imaging with 50% bandwidth transducers.

One may reasonably ask the question: why does the time of flight algorithm work with 50% bandwidth transducers? The answer is that even though the time pulse that travels through the target has only 50% bandwidth, it is still possible to deduce the time delays.

Figure 12:
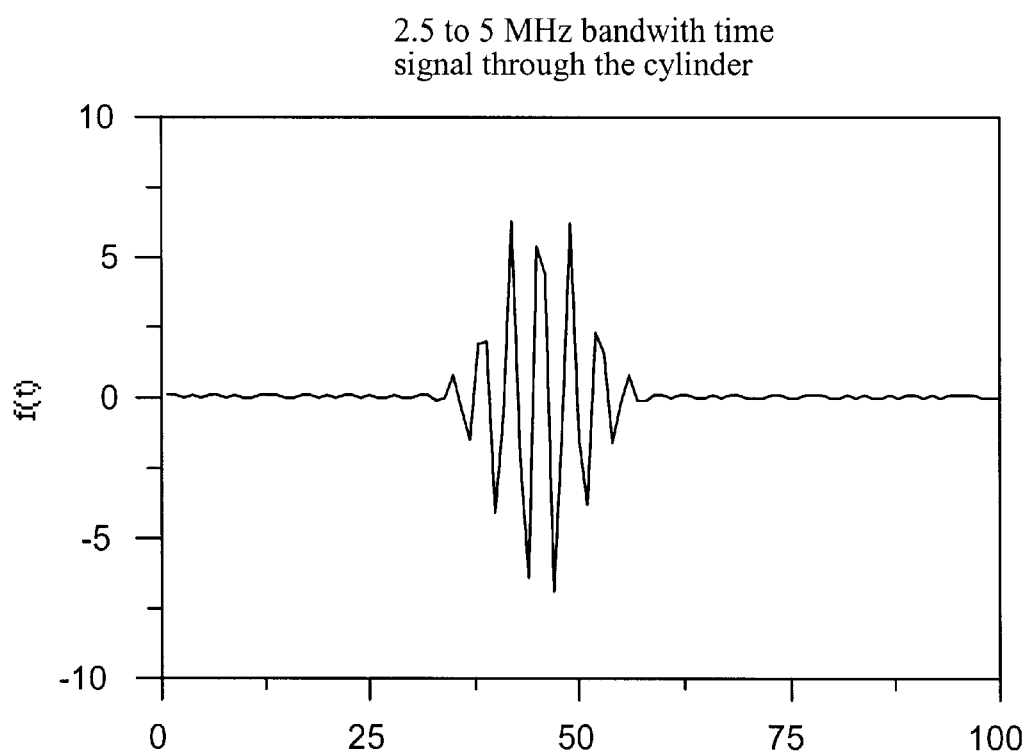
FIG. 12 is the 2.5 MHz to 5 MHz bandwidth time signal through a cylinder.

FIG. 12 shows the time signal computed for a 2.4 cm dia. 1520 m/s cylinder illuminated by a plane wave for 20 frequencies from 2.5 to 5 MHz at a receiver located at the center of the receiving array. The frequency domain data for this case is $f^{total}(\omega)/f^{inc}(\omega)$ which was then transformed to time. Note that this division by $f^{inc}$ in the frequency domain removes the time delay due to the propagation from source to receiver through the background medium (water 1500 m/s) and so the center of the time pulse gives the time shift due to the cylinder.

Suppose now that we attempted to find the center of the waveform in FIG. 12 with a optimization algorithm (say Newton's method) starting with t=0 (index 51) as the starting guess. Further suppose that we defined the center as coincident with the maximum wave magnitude.

Figure 13:
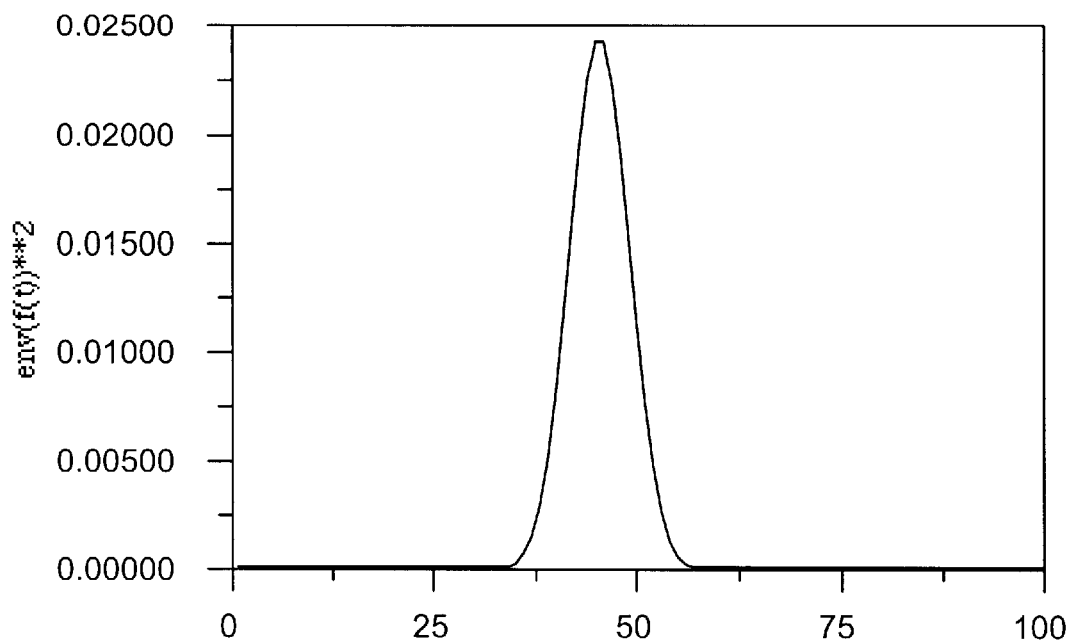
FIG. 13 is the squared envelope of the 2.5 MHz to 5 MHz bandwidth time signal through a cylinder.

Clearly we would find the negative peak near index 51—a local maximum. This is analogous to what happens with the parabolic inversion algorithm starting with a zero guess. The time of flight algorithm, on the other hand, finds the time delay by first taking the envelope of the waveform. The envelope squared of the signal shown in FIG. 12 is shown in FIG. 13.

It is now a simple matter to find the time delay to the waveform center with either an optimization algorithm or by simply detecting the index of the maximum value.

The preceding discussion suggests that the parabolic inversion algorithm might avoid local minima, even with 50% bandwidth transducers, if one operated on the envelope of the time waveform as the data. It is a simple matter to take the frequency domain output of the parabolic algorithm, transform to time, and then take the envelope. Unfortunately, the envelope operator is not differentiable and the parabolic inversion algorithm relies on gradient direction optimization (conjugate gradients). This difficulty can, however, be overcome by making the square of the envelope the time domain output data. This function is differentiable and a conjugate gradient optimization algorithm can be applied. Specifically, the new functional to be minimized is:

$$F[\gamma]=\|env(f^{parabolic}(\gamma,t))^2-env(f^{data}(t))^2\|^{22.1}$$

(with multiple receivers and views of course). Derivation of the Jacobian and its adjoint for the new functional is straightforward. The resulting forward scattering calculations and the Jacobian and its adjoint are best viewed in the following pseudo code form.

C.4.a. PseudoCode for time domain parabolic code algorithm:

For the time domain code, we first set the parameter $\Delta f$=the frequency domain sample interval so that the total time period T=1./$\Delta f$ is sufficient to contain the minimum and maximum time shifts in the data. We then specify the minimum and maximum frequencies by their indices nmin and nmax:

fmin=minimum frequency=nmin $\Delta f$, fmax=maximum frequency=nmax $\Delta f$, using the desired fmax and fmin.

We then select the number of time steps, nt>nmax and set the time domain sample interval as: $\Delta t$=1/(nt $\Delta f$). Then, nf=the number of frequencies, is set=nmax−nmin+1 and the frequency list is set as:

freq(lf)=(lf−1+nmin)$\Delta f$, lf=1, . . . ,nf

Now, suppose that the array fc(nr,nv,nf) contains the frequency domain total field computed by the parabolic algorithm for nr receivers and nv views and let the array fi$\omega$(nr,nf) contain the incident field for the parabolic algorithm. We then transform this frequency domain to the envelope squared of the time domain data via the operations:

for lv=1, . . . ,nv
      for lr=1, . . . ,nr
        fctemp(i)=0, i=1, . . . ,nt
        for lf=1, . . . ,nf
          fctemp(lf+nmin)=(fc(lr,lv,lf)/fi$\omega$(lr,lf)) wt(lf)
        next lf
        fctemp→FFT$^{-1}_{nt}$\{fctemp\}
        for n=1, . . . ,nt
          f$\omega$(lr,lv,n)=fctemp(n)
          f(lr,lv,n)=fctemp(n) fctemp*(n)
        next n
      next lr
    next lv Now, f(nr,nv,nt) contains the time envelope squared of the simulated signals. Note we have also computed the array f$\omega$(nr,nv,nt) which contains the complex analytic time domain waveforms. This function is needed for the Jacobian and Jacobian adjoint calculations. The frequency domain filter wt(nf) is given by:

freqc=(fmax+fmin)/2 freqb=(fmax−fmin)/2 wt(lf)=(0.42+0.5 cos($\pi$(freq(lf)−freqc)/freqb)+0.08 cos (2$\pi$(freq(lf)−freqc)/freqb))

*exp(−i2$\pi$freq(lf)$\Delta t$ (nt/2)), lf=1, . . . ,nf and is applied to prevent sidelobes in the envelope and to shift the time=0 index in the array from 1 to nt/2+1.

In order to compute the gradient (Jacobian adjoint operating on the residual), we first compute the time domain residual array:

$$r(lr,lv,lt)=f^{data}(lr,lv,lt)-f(lr,lv,lt),\ lt=1,\ldots,nt,\ lv=1,\ldots,lv,\ lr=1,\ldots,nr$$

we then compute the frequency domain residual, r$\omega$(nr,nv,nf) by the calculation:

for lv=1, . . . ,nv
      for lr=1, . . . ,nr
        for n=1, . . . ,nt
          fctemp(n)=2 r(lr,lv,n) f$\omega$(lr,lv,n)
        next n
        fctemp→FFT$_{nt}$\{fctemp\}
        for lf=1, . . . ,nf
          r$\omega$(lr,lv,lf)=fctemp(lf=nmin) (wt(lf)/fi$\omega$(lr,lf))*
        next lf
      next lr
    next lv Once the frequency domain residual array is computed, we then apply the original Jacobian adjoint of the frequency domain parabolic algorithm:

$\nabla F = J$(frequency domain parabolic Jacobian)$^H \cdot r\omega$

The Jacobian operating on a perturbation to $\gamma$ (which is also needed to perform a conjugate gradient optimization) s similarly computed.

Note on the Jacobian implementation: observe that the operation of converting to time domain data, then taking the envelope and squaring is concatenated onto the operation of propagating the fields via the parabolic algorithm at the respective frequencies, therefore, it follows that the implementation of the Jacobian will follow from the standard chain rule of vector calculus. This implementation is in fact given explicitly in the above pseudo-code, but is restated explicitly here for further elucidation of the process.

C.4.b. Conclusion:

We have implemented this enveloped time domain parabolic algorithm and have verified that it does indeed converge from a zero starting guess. The final image is somewhat degraded (lower resolution) relative to the frequency domain algorithm with a good starting guess due to the loss of some information from the envelope operation. However, this code does produce a sufficiently accurate starting guess for the frequency domain algorithm which can then refine the resolution of the image.

The invention comprises several methods as listed below:

W-1. (Multiple Wavelength (n$\lambda$) Pixels) A method for producing an image of an object in a region from wavefield energy that has been transmitted into and scattered by the object, said image comprising a map of selected physical characteristics at selected points within the region, said image being stored in a computer memory, and said method comprising the steps of:

(a) transducing an electric signal at each of one or more frequencies into wavefield energy propagated with respective wavelengths from one or more of transmitter transducer positions, each said transmitter transducer position propagating wavefield energy at at least one orientation defined by Euler angles with respect to a selected fixed coordinate system;

(b) for one or more receiver positions each having at least one orientation defined by Euler angles with respect to said selected fixed coordinate system, detecting at each of said one or more receiver positions and respective orientations thereof said wavefield energy;

(c) electronically processing said detected wavefield energy so as to transform said detected wavefield energy into one or more reception stored signals stored in said computer memory and corresponding to a scattered wavefield energy detected;

(d) setting a region characteristics estimate of selected physical characteristics at selected points within the region and storing each said region characteristics estimate in said computer memory;

(e) performing a convergence step comprising the following steps:
- (1) preparing, for each said one or more frequencies at each said transmitter transducer positions and respective orientations thereof; an estimate of a total wavefield energy at said selected points derived from a selected incident wavefield energy for said selected points stored in the computer memory and said region characteristics estimate for said selected points by the steps of:
  - (i) designating a primary set of surfaces of a plurality of selected surfaces, said selected surfaces being-separated one from another by, and a different secondary set of surfaces of said selected surfaces, each said selected surface intersecting said region;
  - (ii) setting the estimate of the total wavefield energy equal to an initial total incident wavefield energy estimate for the primary set of surfaces;
  - (iii) computing the estimate of the total wavefield energy on the secondary set of surfaces using the region characteristics estimate on the union of the primary and secondary sets of surfaces and the total wavefield energy on the primary set of surfaces;
  - (iv) re-designating the primary set of surfaces to include a sub- set of the secondary set of surfaces and re-designating the secondary set of surfaces to include another set of the selected surfaces; and
  - (v) repeating steps ((iii) through ((iv)) until the estimate of the total wavefield energy is computed for each of the selected surfaces;
- (2) deriving, for each of said one or more frequencies at each said transmitter transducer position and orientations thereof; a calculated scattered wavefield energy for one or more of said receiver positions and respective orientations thereof from at least one of said region characteristics estimate at said selected points and said estimate of said total wavefield energy for a corresponding transmitter transducer position and orientations thereof at said selected points by performing the steps of:
  - (i) for each selected point of a portion of the selected points, said potion of the selected points corresponding to one of said one or more receiver positions and respective orientations thereof; setting said calculated scattered wavefield energy equal to the estimate of the total wavefield energy less said selected incident wavefield energy; and
  - (ii) computing a sum over said portion of said selected points equal to the sum of the calculated scattered wavefield energy for said portion of said selected points times a function constructed to correspond to one or more of said one or more receiver positions and respective orientations thereof;
- (3) for each said transmitter transducer position and orientations thereof and for each said receiver position and orientation thereof comparing said scattered wavefield energy detected to said calculated scattered wavefield energy to derive therefrom a comparator; and
- (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:
  - (i) at each said one or more frequencies, said estimate of said total wavefield energy for said selected points for each of said one or more of said transmitter transducer positions and respective orientations thereof;
  - (ii) at each of said one or more frequencies, said calculated scattered wavefield energy for said one or more receiver positions and respective orientations thereof; and for each of said one or more of said transmitter transducer positions and respective orientations thereof;
  - (iii) at each of said one or more frequencies, said scattered wavefield energy detected for said one or more receiver positions and respective orientations thereof and for each of said one or more of said transmitter transducer positions and respective orientations thereof; and
  - (iv) said region characteristics estimate for said selected points;

(f) repeating said convergence step until said comparator is less than or equal to said selected tolerance, and thereafter storing said region characteristics estimate as said image in the computer memory.

X1. (Two opposing Compression plates) A method for producing an image of an object in human breast tissue from wavefield energy that has been transmitted into and scattered by the object in the human breast tissue, said image comprising a map of selected physical characteristics at selected points within the human breast tissue, said image being stored in a computer memory, and said method comprising the steps of:

compressing a human breast between two opposing plates;
- (a) transducing an electric signal at each of one or more frequencies into wavefield energy propagated from one or more of transmitter transducer positions;
transmitting wavefield energy into one plate, through the human breast tissue, and out of the other plate;
- (b) detecting, outside the other plate, at each of said one or more receiver positions a detected wavefield energy;
- (c) electronically processing said detected wavefield energy so as to transform said detected wavefield energy into one or more reception stored signals stored in said computer memory and corresponding to a scattered wavefield energy detected;
- (d) setting a region characteristics estimate of selected physical characteristics at selected points within the region and storing each said region characteristics estimate in said computer memory;
- (e) performing a convergence step comprising the following steps:
  - (1) preparing, for each said one or more frequencies at each said transmitter transducer position, an estimate of a total wavefield energy at said selected points derived from a selected incident wavefield energy for said selected points stored in the computer memory and said region characteristics estimate for said selected points by the steps of:
- (i) designating a primary set of surfaces of a plurality of selected surfaces and a different secondary set of surfaces of said selected surfaces, each said selected surface intersecting said region;
- (ii) setting the estimate of the total wavefield energy equal to an initial total incident wavefield energy estimate for the primary set of surfaces;
- (iii) computing the estimate of the total wavefield energy on the secondary set of surfaces using the region characteristics estimate on the union of the primary and secondary sets of surfaces and the total wavefield energy on the primary set of surfaces;
- (iv) re-designating the primary set of surfaces to include a sub-set of the secondary set of surfaces and re-designating the secondary set of surfaces to include another set of the selected surfaces; and
- (v) repeating steps ((iii) through ((iv)) until the estimate of the total wavefield energy is computed for each of the selected surfaces;

(2) deriving, for each of said one or more frequencies at each said transmitter transducer position, a calculated scattered wavefield energy for one or more of said receiver positions from at least one of said region characteristics estimate at said selected points and said estimate of said total wavefield energy for a corresponding transmitter transducer position at said selected points by performing the steps of:
- (i) for each selected point of a portion of the selected points, said potion of the selected points corresponding to one of said one or more receiver positions, setting said calculated scattered wavefield energy equal to the estimate of the total wavefield energy less said selected incident wavefield energy; and
- (ii) computing a sum over said portion of said selected points equal to the sum of the calculated scattered wavefield energy for said portion of said selected points times a function constructed to correspond to one or more of said one or more receiver positions;

(3) for each said transmitter transducer position and for each said receiver position, comparing said scattered wavefield energy detected to said calculated scattered wavefield energy to derive therefrom a comparator; and (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:
- (i) at each said one or more frequencies, said estimate of said total wavefield energy for said selected points for each of said one or more of said transmitter transducer positions and respective orientations thereof;
- (ii) at each of said one or more frequencies, said calculated scattered wavefield energy for said one or more receiver positions and respective orientations thereof; and for each of said one or more of said transmitter transducer positions and respective orientations thereof;
- (iii) at each of said one or more frequencies, said scattered wavefield energy detected for said one or more receiver positions and respective orientations thereof; and for each of said one or more of said transmitter transducer positions and respective orientations thereof; and
- (iv) said region characteristics estimate for said selected points; repeating said convergence step until said comparator is less than or equal to said selected tolerance, and thereafter storing said region characteristics estimate as said image in the computer memory.

X2. (reflecting end plates)
The method as defined in Claim X1,
Compressing the breast between a third and fourth opposing plates; said four plates being respectively orthogonally oriented;
Wherein the third and fourth plates reflect the propagated wavefield energy.

Y1. (transducing four plates) A method for producing an image of human breast tissue from wavefield energy that has been transmitted into and scattered by the human breast tissue, said image comprising a map of selected physical characteristics at selected points within the human breast tissue, said image being stored in a computer memory, and said method comprising the steps of:
compressing human breast tissue between two pairs of opposing plates;
- (a) transducing an electric signal at each of one or more frequencies into wavefield energy propagated from one or more of transmitter transducer positions;
transmitting wavefield energy into one or more of the plates, through the human breast tissue, and out of the one or more the other plates;
- (b) detecting, outside one or more plates, at each of said one or more receiver positions a detected wavefield energy;
- (c) electronically processing said detected wavefield energy so as to transform said detected wavefield energy into one or more reception stored signals stored in said computer memory and corresponding to a scattered wavefield energy detected;
- (d) setting a region characteristics estimate of selected physical characteristics at selected points within the region and storing each said region characteristics estimate in said computer memory;
- (e) performing a convergence step comprising the following steps:
  - (1) preparing, for each said one or more frequencies at each said transmitter transducer position, an estimate of a total wavefield energy at said selected points derived from a selected incident wavefield energy for said selected points stored in the computer memory and said region characteristics estimate for said selected points by the steps of:
   (i) designating a primary set of surfaces of a plurality of selected surfaces and a different secondary set of surfaces of said selected surfaces, each said selected surface intersecting said region;
   (ii) setting the estimate of the total wavefield energy equal to an initial total incident wavefield energy estimate for the primary set of surfaces;
   (iii) computing the estimate of the total wavefield energy on the secondary set of surfaces using the region characteristics estimate on the union of the primary and secondary sets of surfaces and the total wavefield energy on the primary set of surfaces;
   (iv) re-designating the primary set of surfaces to include a sub-set of the secondary set of surfaces and re-designating the secondary set of surfaces to include another set of the selected surfaces; and
   (v) repeating steps ((iii) through ((iv)) until the estimate of the total wavefield energy is computed for each of the selected surfaces;
(2) deriving, for each of said one or more frequencies at each said transmitter transducer position, a calculated scattered wavefield energy for one or more of said receiver positions from at least one of said region characteristics estimate at said selected points and said estimate of said total wavefield energy for a corresponding transmitter transducer position at said selected points by performing the steps of:
   (i) for each selected point of a portion of the selected points, said potion of the selected points corresponding to one of said one or more receiver positions, setting said calculated scattered wavefield energy equal to the estimate of the total wavefield energy less said selected incident wavefield energy; and
   (ii) computing a sum over said portion of said selected points equal to the sum of the calculated scattered wavefield energy for said portion of said selected points times a function constructed to correspond to one or more of said one or more receiver positions;
(3) for each said transmitter transducer position and for each said receiver position, comparing said scattered wavefield energy detected to said calculated scattered wavefield energy to derive therefrom a comparator; and
(4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:
   (i) at each said one or more frequencies, said estimate of said total wavefield energy for said selected points for each of said one or more of said transmitter transducer positions and respective orientations thereof;
   (ii) at each of said one or more frequencies, said calculated scattered wavefield energy for said one or more receiver positions and respective orientations thereof and for each of said one or more of said transmitter transducer positions and respective orientations thereof;
   (iii) at each of said one or more frequencies, said scattered wavefield energy detected for said one or more receiver positions and respective orientations thereof and for each of said one or more of said transmitter transducer positions and respective orientations thereof; and
   (iv) said region characteristics estimate for said selected points;
   (v)
(f) repeating said convergence step until said comparator is less than or equal to said selected tolerance, and thereafter storing said region characteristics estimate as said image in the computer memory.

X2. (reflecting end plates)
The method as defined in Claim X1,
Compressing the breast between a third and fourth opposing plates; said four plates being respectively orthogonally;
Wherein the third and fourth plates reflect the propagated wavefield energy.

X1–2. (moving xducers on two plates)
The method as in Claim x1, wherein transmitting wavefield energy into one plate, through the human breast tissue, and out of the other plate further comprises:
   includes transmitting wavefield energy through a portion of said one plate through the human breast tissue, and out of the other plate;
   and repeating until Y1. (transducing four plates) A method for producing an image of human breast tissue from wavefield energy that has been transmitted into and scattered by the human breast tissue, said image comprising a map of selected physical characteristics at selected points within the human breast tissue, said image being stored in a computer memory, and said method comprising the steps of:
   compressing human breast tissue between two pairs of opposing plates;
   (a) transducing an electric signal at each of one or more frequencies into wavefield energy propagated from one or more of transmitter transducer positions;
   transmitting wavefield energy into one or more of the plates, through the human breast tissue, and out of the one or more the other plates;
   (b) detecting, outside one or more plates, at each of said one or more receiver positions a detected wavefield energy;
   (c) electronically processing said detected wavefield energy so as to transform said detected wavefield energy into one or more reception stored signals stored in said computer memory and corresponding to a scattered wavefield energy detected;
   (d) setting a region characteristics estimate of selected physical characteristics at selected points within the region and storing each said region characteristics estimate in said computer memory;

(e) performing a convergence step comprising the following steps:
  (1) preparing, for each said one or more frequencies at each said transmitter transducer position, an estimate of a total wavefield energy at said selected points derived from a selected incident wavefield energy for said selected points stored in the computer memory and said region characteristics estimate for said selected points by the steps of:
    (i) designating a primary set of surfaces of a plurality of selected surfaces and a different secondary set of surfaces of said selected surfaces, each said selected surface intersecting said region;
    (ii) setting the estimate of the total wavefield energy equal to an initial total incident wavefield energy estimate for the primary set of surfaces;
    (iii) computing the estimate of the total wavefield energy on the secondary set of surfaces using the region characteristics estimate on the union of the primary and secondary sets of surfaces and the total wavefield energy on the primary set of surfaces;
    (iv) re-designating the primary set of surfaces to include a sub-set of the secondary set of surfaces and re-designating the secondary set of surfaces to include another set of the selected surfaces; and
    (v) repeating steps ((iii) through ((iv)) until the estimate of the total wavefield energy is computed for each of the selected surfaces;
  (2) deriving, for each of said one or more frequencies at each said transmitter transducer position, a calculated scattered wavefield energy for one or more of said receiver positions from at least one of said region characteristics estimate at said selected points and said estimate of said total wavefield energy for a corresponding transmitter transducer position at said selected points by performing the steps of:
    (i) for each selected point of a portion of the selected points, said potion of the selected points corresponding to one of said one or more receiver positions, setting said calculated scattered wavefield energy equal to the estimate of the total wavefield energy less said selected incident wavefield energy; and
    (ii) computing a sum over said portion of said selected points equal to the sum of the calculated scattered wavefield energy for said portion of said selected points times a function constructed to correspond to one or more of said one or more receiver positions;
  (3) for each said transmitter transducer position and for each said receiver position, comparing said scattered wavefield energy detected to said calculated scattered wavefield energy to derive therefrom a comparator; and
  (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:
    (i) at each said one or more frequencies, said estimate of said total wavefield energy for said selected points for each of said one or more of said transmitter transducer positions and respective orientations thereof;
    (ii) at each of said one or more frequencies, said calculated scattered wavefield energy for said one or more receiver positions and respective orientations thereof and for each of said one or more of said transmitter transducer positions and respective orientations thereof;
    (iii) at each of said one or more frequencies, said scattered wavefield energy detected for said one or more receiver positions and respective orientations thereof, and for each of said one or more of said transmitter transducer positions and respective orientations thereof; and
    (iv) said region characteristics estimate for said selected points;
(h) repeating said convergence step until said comparator is less than or equal to said selected tolerance, and thereafter storing said region characteristics estimate as said image in the computer memory.

Definitions

Definition 1. An inverse scattering imaging method is any imaging method which totally or partially uses wave equation modeling and which utilizes a nonlinear operator relating the inversion data to the image components.

Definition 2. The inversion data is defined by that transformation of the wavefield data which is the range of the nonlinear operator. The domain of the nonlinear operator is the image components.

Definition 3. A parabolic propagation step is an arithmetic operation which computes the wavefield on a set of surfaces given the wavefield on another, disjoint set of surfaces using a parabolic differential (or difference?) equation in the derivation of the arithmetic operation.

Definition 4. By $\lambda$ we mean the wavelength in the imbedding medium for the maximum temporal frequency in the wavefield energy.

Definition 5. By $\Delta$ we mean the average spatial separation of the points used to discretize the discretized wavefield in the computer implementation of the method.

Definition 6. By a short convolution operation we mean a discrete convolution which is faster if done by direct summation rather than by FFT.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed as desired to be secured by United States Letters Patent is:

1. Any inverse scattering imaging method which employs a parabolic propagation step that is accelerated in speed by employing $\Delta > \lambda/2$.

2. Any inverse scattering imaging method as defined in claim 1 which utilizes a compression plate.

3. Any method as in claim 1 which is accelerated in speed by employing a short convolution operation to implement the parabolic propagation step.

4. Any inverse scattering imaging method as defined in claim 3 which utilizes a compression plate.

5. Any inverse scattering imaging method which uses the envelope of the time domain data as the inversion data.

6. Any inverse scattering imaging method as defined in claim 5 which utilizes a compression plate.

7. Any inverse scattering imaging method as defined in claim 5 that is accelerated in speed by employing $\Delta > \lambda/2$ and which also includes a parabolic propagation step.

8. Any inverse scattering imaging method as defined in claim 7 which utilizes a compression plate.

9. Any inverse scattering imaging method as defined in claim 7 that is accelerated in speed by employing a short convolution operation to implement the parabolic propagation step.

10. Any inverse scattering imaging method as defined in claim 9 which utilizes a compression plate.

11. Any inverse scattering imaging method as defined in claim 5 that is accelerated in speed by employing $\Delta > \lambda/2$.

12. Any inverse scattering imaging method as defined in claim 11 that is accelerated in speed by employing a short convolution operation to implement the parabolic propagation step.

13. Any inverse scattering imaging method as defined in claim 12 which utilizes a compression plate.

14. Any method as in claim 5 that uses any function of the envelope of the time domain data as the inversion data such that the resulting inversion data is differentiable with respect to the image.

15. Any method as in claim 5 or 14 which also includes a parabolic propagation step.

16. Any inverse scattering imaging method as defined in claim 14 which utilizes a compression plate.

17. Any inverse scattering imaging method as defined in claim 14 that is accelerated in speed by employing $\Delta > \lambda/2$ and which also includes a parabolic propagation step.

18. Any inverse scattering imaging method as defined in claim 17 which utilizes a compression plate.

19. Any inverse scattering imaging method as defined in claim 17 that is accelerated in speed by employing a short convolution operation to implement the parabolic propagation step.

20. Any inverse scattering imaging method as defined in claim 19 which utilizes a compression plate.

21. Any inverse scattering imaging method as defined in claim 14 that is accelerated in speed by employing $\Delta > \lambda/2$.

22. Any inverse scattering imaging method as defined in claim 21 which utilizes a compression plate.

23. Any inverse scattering imaging method as defined in claim 21 that is accelerated in speed by employing a short convolution operation to implement the parabolic propagation step.

24. Any inverse scattering imaging method as defined in claim 23 which utilizes a compression plate.

25. Any inverse scattering imaging method which utilizes a compression plate.

26. Any method as in claim 25 which also utilizes a parabolic propagation step.

* * * * *